(12) United States Patent
Tihon

(10) Patent No.: US 6,743,198 B1
(45) Date of Patent: Jun. 1, 2004

(54) SELF-CLEANSING BLADDER DRAINAGE DEVICE

(75) Inventor: Claude Tihon, Eden Prairie, MN (US)

(73) Assignee: ContiCare Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/313,083

(22) Filed: Jun. 22, 1999

Related U.S. Application Data

(63) Continuation-in-part of application No. 08/960,136, filed on Oct. 29, 1997, now abandoned, which is a continuation-in-part of application No. 08/579,592, filed on Dec. 26, 1995, now Pat. No. 5,738,654, which is a continuation-in-part of application No. 08/407,297, filed on Mar. 20, 1995, now Pat. No. 5,562,622.

(51) Int. Cl.[7] ............................................. A61M 29/00
(52) U.S. Cl. .................. 604/104; 604/170.03; 604/174
(58) Field of Search ................................ 604/506, 507, 604/508, 509, 510, 513, 517, 93.01, 544, 104–107, 245, 329, 349, 350, 174, 177–180, 264, 523, 43, 265, 274, 275, 276, 530, 533–536, 537, 540, 170.03; 606/193, 198; 128/836

(56) References Cited

U.S. PATENT DOCUMENTS

| | | | |
|---|---|---|---|
| 2,450,217 A | | 9/1948 | Alcorn |
| 3,260,258 A | | 7/1966 | Berman |
| 3,769,981 A | | 11/1973 | McWhorter |
| 3,811,450 A | | 5/1974 | Lord |
| 3,815,608 A | * | 6/1974 | Spinosa et al. ............. 604/105 |
| 4,307,723 A | * | 12/1981 | Finney ..................... 604/544 |
| 4,501,580 A | | 2/1985 | Glassman |
| 4,643,720 A | * | 2/1987 | Lanciano .................. 604/95.04 |
| 4,645,493 A | * | 2/1987 | Ferrando et al. ........... 604/174 |
| 4,723,946 A | | 2/1988 | Kay |
| 4,738,667 A | * | 4/1988 | Galloway ................... 604/530 |
| 4,740,195 A | * | 4/1988 | Lanciano .................... 604/533 |
| 5,049,140 A | | 9/1991 | Brenner et al. |
| 5,141,502 A | * | 8/1992 | Macaluso, Jr. .............. 604/528 |
| 5,176,664 A | | 1/1993 | Weisman |
| 5,282,784 A | * | 2/1994 | Willard ..................... 604/544 |
| 5,523,092 A | * | 6/1996 | Hanson et al. .............. 424/423 |

FOREIGN PATENT DOCUMENTS

| | | |
|---|---|---|
| DE | 4134030 | 4/1993 |
| EP | 326908 | 8/1989 |
| GB | 2166958 | 5/1986 |

\* cited by examiner

*Primary Examiner*—LoAn H. Thanh
(74) *Attorney, Agent, or Firm*—Thomas J. Nikolai; Nikolai & Mersereau, P.A.

(57) ABSTRACT

An urethral drain having deep external drainage channels, a low-profiled bladder retention segment, and a reversibly detachable collection segment, facilitates the draining of urine and fluids from the bladder. The low-profiled retention means minimizes bladder irritations and the deep external channels reduce the occurrence of infections. Incorporation of a reduced diameter smooth segment on the catheter, proximate the location of the external urethral sphincter allows the patient to void normally and at will. Modifying the size of this smooth segment aids the function of a defective sphincter in controlling urine leakage. The drain can be worn concealed within the urethra. Flushing action from normal voiding washes out particulate matters in the urethra and the concealed drain further minimizes contamination. Together, these features improve quality of life for patients needing catheterization.

18 Claims, 21 Drawing Sheets

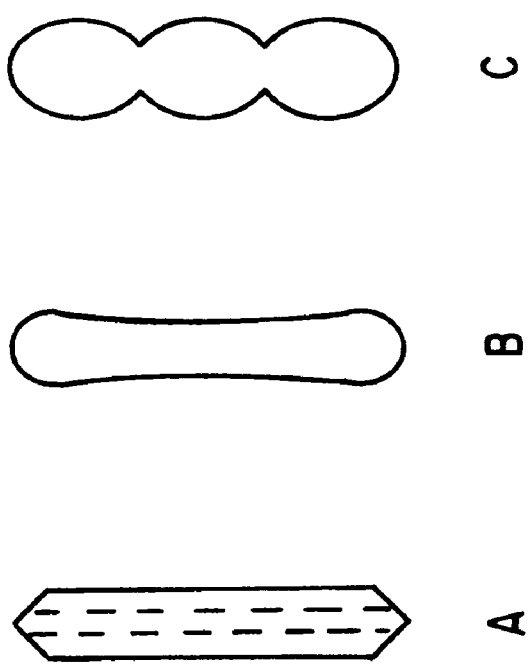

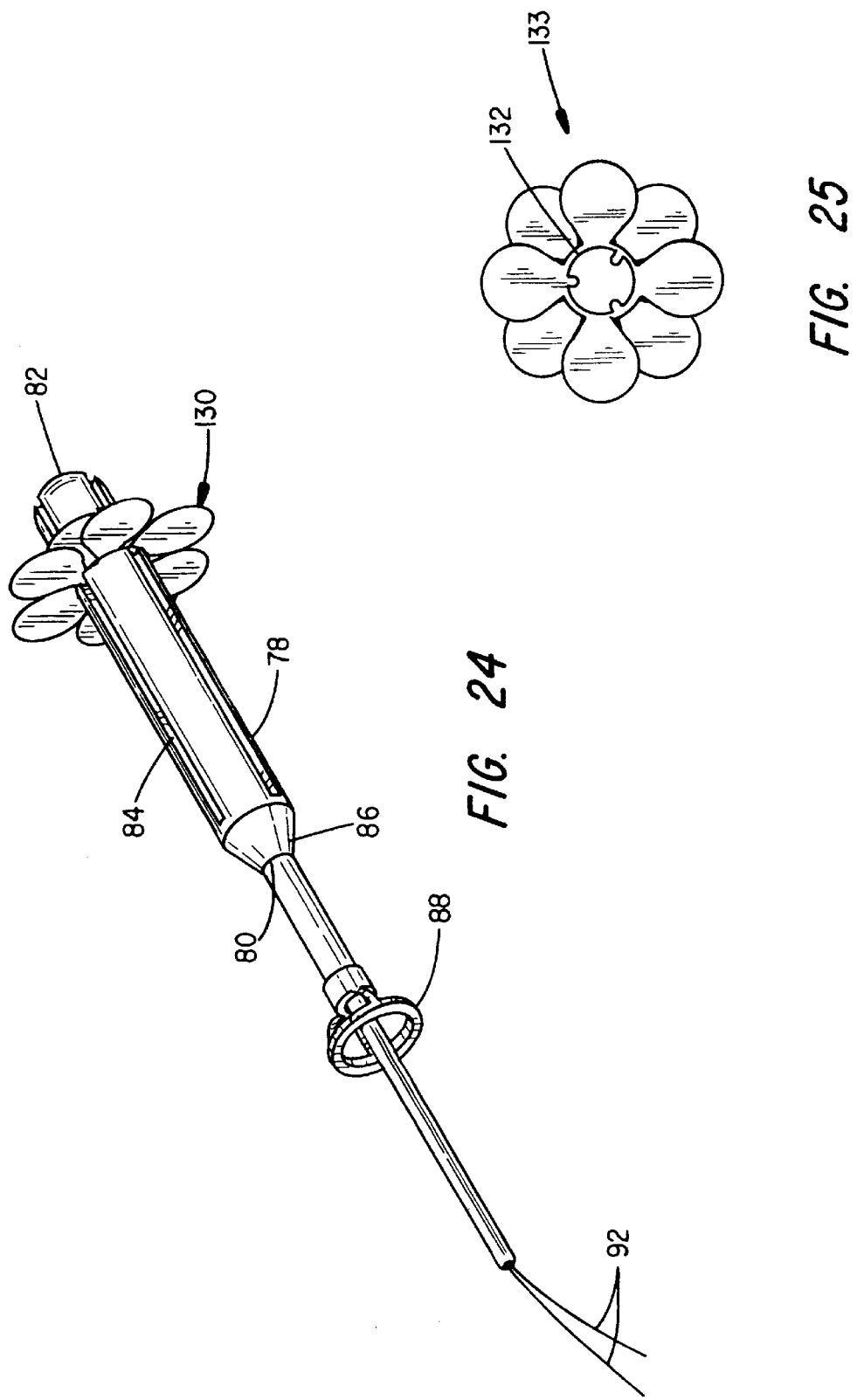

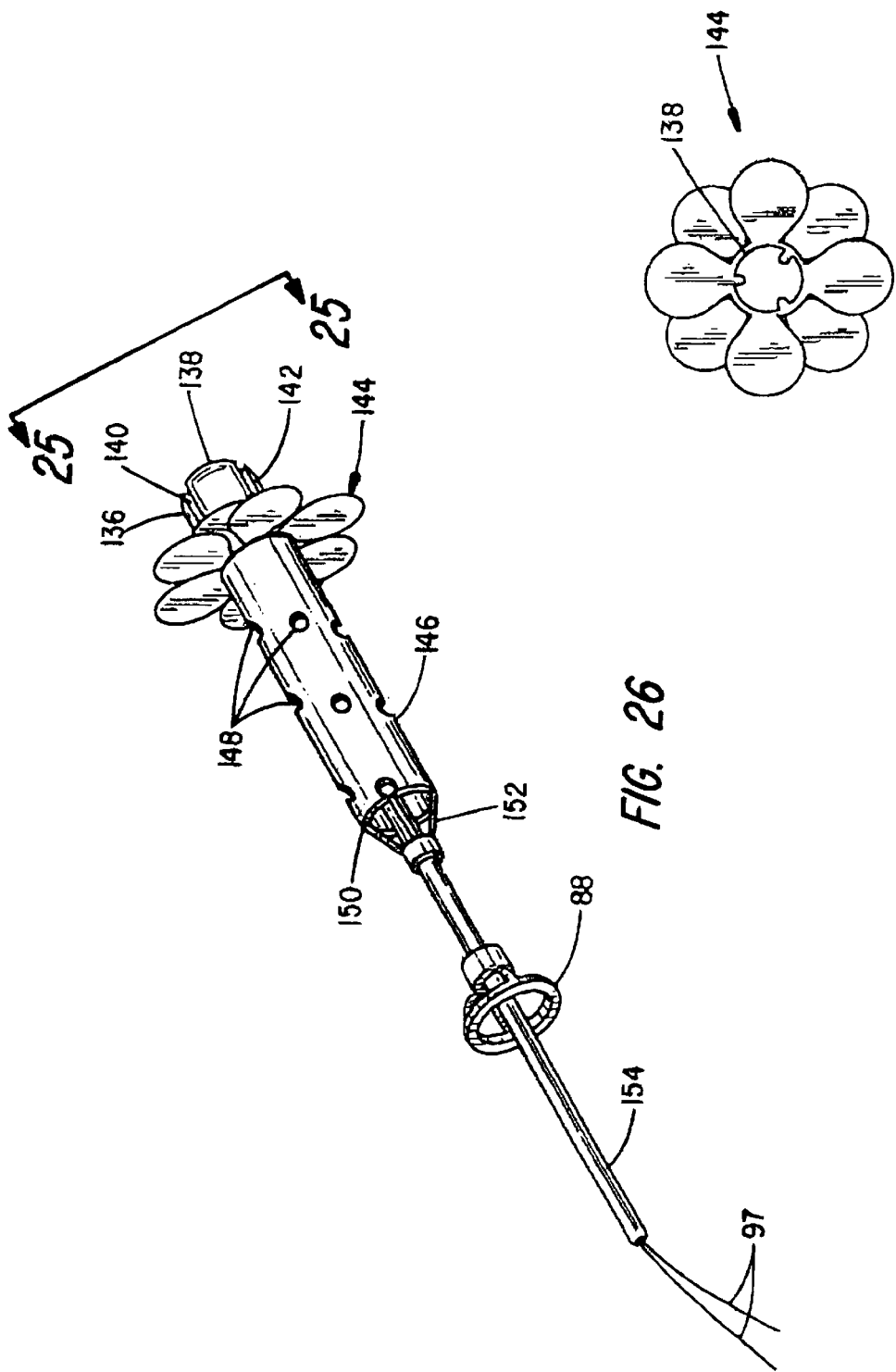

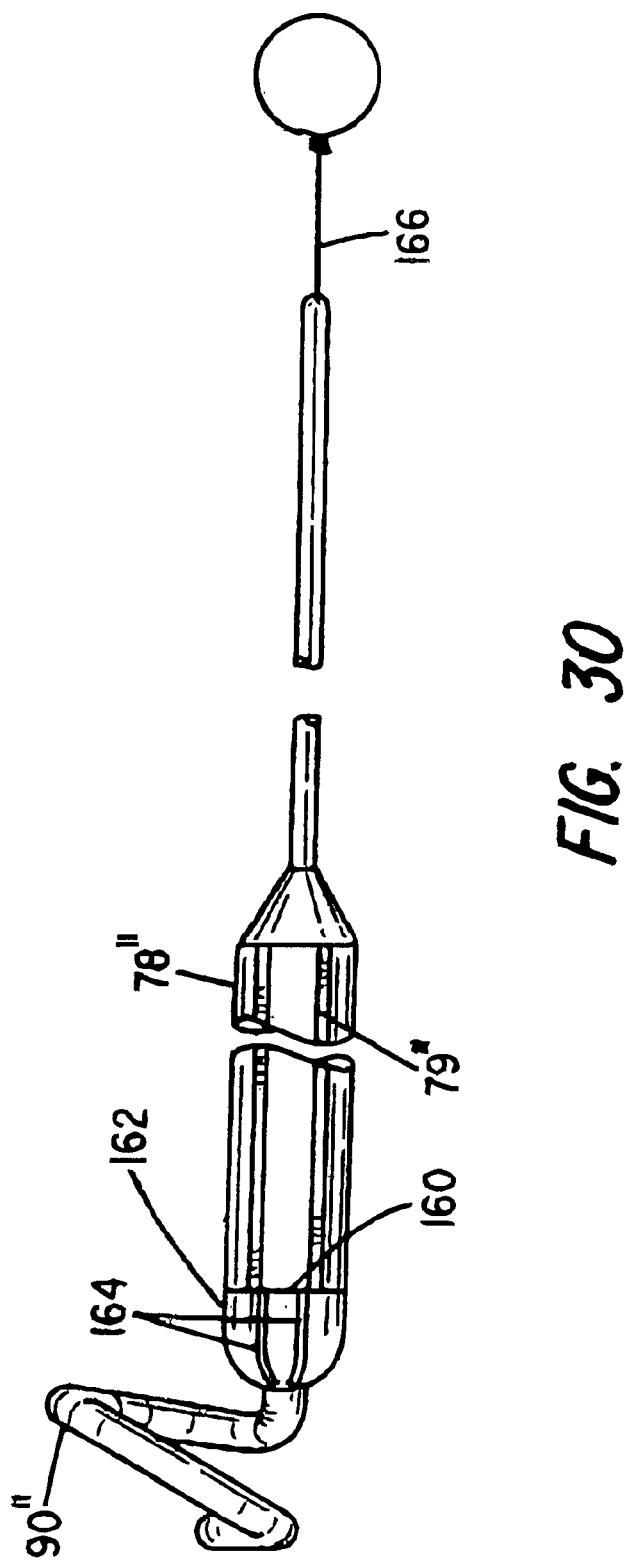

SELF-CLEANSING BLADDER DRAINAGE DEVICE

CROSS REFERENCE TO RELATED APPLICATION

This application is a continuation-in-part of application Ser. No. 08/960,136, filed Oct. 29, 1997, (now abandoned), which is a continuation-in-part of application Ser. No. 08/579,592, filed Dec. 26, 1995 (now U.S. Pat. No. 5,738, 654), which is a continuation-in-part of application Ser. No. 08/407,297, filed Mar. 20, 1995 (now U.S. Pat. No. 5,562, 622), and entitled "SELF-CLEANSING BLADDER DRAINAGE DEVICE".

BACKGROUND OF THE INVENTION

1. Field of the Invention

This invention relates generally to body fluid drainage devices, and more particularly to a urinary drain having improved performance characteristics.

2. Discussion of the Prior Art

Urethral catheters, such as the Foley catheter, now used for bladder drainage are essentially elongated tubular structures placed in the urethra for draining urine through the central lumen thereof. Near the distal end of the tube is an inflatable balloon which, when inflated while in the bladder, allows the catheter to be held in place. Its proximal end has a drainage port as well as a balloon inflation port. The proximal end of the catheter protrudes beyond the urethral orifice and can be attached to a bag receptacle for the collection of the near constantly dripping urine from the bladder. The collection bag is either-attached to the patient's leg when the patient is ambulatory, or to the side of the bed during bed rest. At times, a plug is used in place of the bag to stop the leakage of urine from the catheter tip.

When Foley catheters or the like are used, patients are not able to void when they want to. Rather, urine is continuously drained from the bladder through the central lumen of the elongated tube and into the collection bag. Ambulatory patients are therefore obligated to have the leg bag attached to their leg, and this poses a source of great inconvenience, unsightliness and problems affecting their quality of life. Due to the fact that urine is continuously being drained from the bladder, the bladder is continuously near empty. The dome of the bladder, therefore, rests continuously on the water-filled bulging balloon retention part of the Foley catheter, causing tissue compression, irritation and erosion related adverse side effect problems. Furthermore, increased urinary tract infection is common with patients using such catheters, especially when used on a chronic basis. Though the causal factors have not been precisely identified, length of time of catheterization has been associated with an increased frequency and severity of urinary tract infection, presumably due to the migration of bacteria up the urethral tract. Frequently, yellow encrusted and mucoid proteinaceous depositions containing bacteria are found on the surfaces of the catheter with much higher concentration on the inner lumen surfaces. The mandated usage of urine receptacles causes additional associated stigma of soiled clothing, furniture and odor.

The Spinosa et al. U.S. Pat. No. 3,815,608 discloses in FIG. 9 thereof a typical Foley urinary catheter having an inflatable balloon 64 for retaining the distal end portion of the catheter with its drainage hole 56 within the urinary bladder. An alternative embodiment disclosed in FIGS. 6 and 7 of the Spinosa et al. patent depicts a urinary catheter that uses a helically threaded region thereof as the retention means in place of an inflatable balloon. This device still relies upon the central lumen 46 as the urine path while the channels 48 define between the helical threads 44 allow for "drainage of exudate discharged from the prostate gland".

SUMMARY OF THE INVENTION

The present invention provides a solution to increase the quality of life for patients who require drainage catheters by solving compression and irritation related problems, giving patients an option to carry on their daily lives more normally and reduce incidence of the common urinary tract infections. One embodiment of the invention comprises a bladder drainage device having at least one deep, open fluid-drainage channels and a low profile bladder retention means at its distal end. In addition, it can contain an essentially smooth segment, preferably narrowed, in the area of the external urethral sphincter. Urine drains from the bladder, via the open surface channels. The narrowed smooth segment permits the external urethral sphincter to function normally to shut off the leakage of urine from the bladder to the lower portion of the urethra. The drainage channels may but need not reappear below the external sphincter. When the sphincter opens, urine and fluid will flow past the relaxed sphincter area at the smooth, narrowed drain region, and down between the narrowed region and the urethral wall. Unlike the situation with the Foley type catheter and the catheter of FIGS. 6 and 7 of the Spinosa et al. '608 patent, where urine is continuously drained in a leaking fashion from the bladder through an internal lumen of the drainage catheter, the present configuration of the invention allows urine to be stored in the bladder until voided in mass, much as in a normal manner, when the patient is ready to do so. Due to this natural and daily multiple automatic flushing action in the urethra and channel walls by a rushing of the bolus of urine, the bladder drain of the present invention is self-cleansing without any added external pressurized flushing equipment means, such as that described in U.S. Pat. No. 4,723,946, or any added steps for the patient.

The device of the present invention, without the smooth segment, can be worn by patients in cases where constant urine drainage is required or unavoidable. Thus, the drain will have the benefits of the lower profile retention means for reduced bladder irritability, and the deep external drainage channel(s) causing urine flow to be in contact with the urethral wall to minimize colonization of bacteria and other contaminants within a lumen, thus lower possibility of infections.

The presence of the narrow, smooth segment at the site of the external urethral sphincter region allows the natural constriction of the external urethral sphincter to terminate the flow of fluid to the distal bulbous and penile urethra as the sphincter normally functions. The patient is, therefore, able to control his own voiding frequency. This permits the drain device to be worn by ambulatory patients without the necessity of an external urine drainage collection leg bag.

Patients suffering from urinary incontinence have differing degrees of contractibility of the external urinary sphincter, depending upon age and other factors. By providing a smooth surface section that can be repositioned along the length of the externally grooved drain member and which can be selected for its outer diameter, a variety of patients can be accommodated.

The distal end of the drain device located within the bladder contains a retention means for retaining it at the bladder neck. This preferably a coiled section of the flexible, deep open channeled drainage device, which is initially straightened for insertion in the urethra by a straightening stylet placed in a central lumen of the drain device. Removing the wire after drain placement restores the curl. Due to the fact that the low profile retention means is an extension of the drainage segment, no balloon is needed, nor is there a necessity for a perpendicular, upward-protruding tubing with lateral openings for the passage of urine. The retention means is spaced apart from the smooth narrowed section a distance to assure drainage within the prostatic urethra. Before exiting the urethra, the deep channels are replaced by a traditional tubular structure, the collection segment, which proceeds to exit the urethra. This collection segment collects fluid from the narrowed drain body or from the deep external channel(s) above, transports it beyond the meatus of the penis, and permits the attachment of a urine drainage collection bag or a plug at the proximal end. The tubular collection segment can be readily detached from the main drain body, thus leaving the entire drain device concealed inside the urethra. This further insures minimal infection from outside contamination, and avoids the aesthetically displeasing and uncomfortable presence of an external device.

Given the anatomical differences between the urinary systems in males and females, and in particular the short length and shape configuration of the female urethra, the drainage device for a female patient preferably comprises a soft, flexible, plastic body member having a flat coil bladder retention means at its distal end and a corresponding retention means at its proximal end to prevent the device from migrating upward into the bladder. The proximal retention device is configured to conform to the vestibule proximate the urethral opening. It is preferably an open structure or perforated to permit exposure of the underlying tissue to air.

In addressing female stress incontinence, a cuff member of a chosen size appropriate for the patient may be placed about the drain member to cooperate with the urinary sphincter, allowing the sphincter to create an improved seal against the cuff to block urine flow.

Thus, the object of this invention is to greatly increase the quality of life for patients who require bladder drainage catheters.

BRIEF DESCRIPTION OF THE DRAWINGS

The foregoing features and advantages of the invention will become apparent to those skilled in the art from the following detailed description of the present invention, in which numerals in the several view refer to corresponding parts.

FIG. 1(a) is a partial view of the bladder drain of FIG. 1, but with an alternative anchoring structure;

FIG. 9(a) is an exploded, partial, sectional view of a drain member having straight (non-spiral) surface grooves and a collection tube used therewith;

FIGS. 15A, B and C illustrate alternative shapes for the cuff member illustrated in FIG. 12;

FIG. 24 is a perspective view of an alternative preferred embodiment of a bladder drain in accordance with the invention and incorporating an alternative bladder retention structure;

FIG. 25 is a top view of the bladder drain of FIG. 24;

FIG. 26 is yet another alternative embodiment of the present invention;

FIG. 27 is a top plan view of the device of FIG. 26;

FIG. 30 is still a further preferred embodiment of the invention.

DETAILED DESCRIPTION OF THE PREFERRED EMBODIMENT

Figure 1:
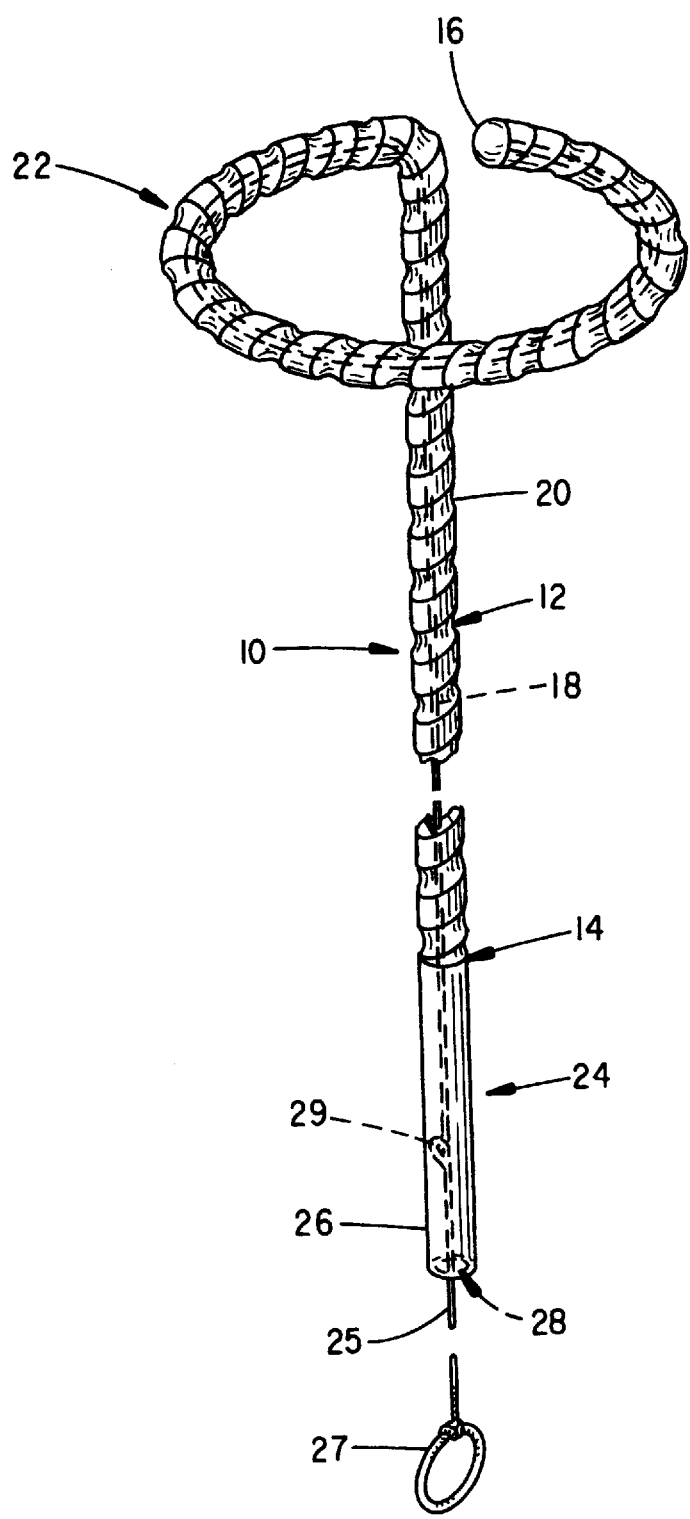
FIG. 1 is an elevational view of a bladder drain in accordance with a first embodiment of the invention.
Figure 1:
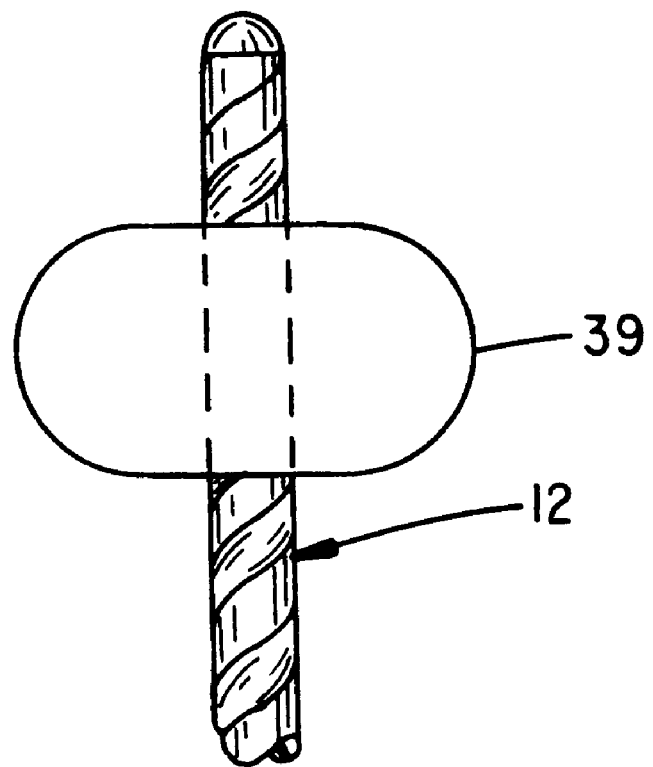

Referring first to FIG. 1, there is shown a perspective view of a bladder drainage device in accordance with a first embodiment of the invention. It is indicated generally by numeral 10 and is seen to comprise an elongated, flexible tubular body member 12 having a proximal end 14 and a distal end 16 and with a stylet receiving lumen 18 extending longitudinally toward but just short of the distal end 16. Thus, the distal end 16 covers the stylet lumen precluding the flow of body fluids therethrough when the drainage device 10 of the present invention is in place within the urethra of a patient.

With continued reference to FIG. 1, the body member 12 of the drainage device 10 is shown as including at least one channel 20 formed in the surface thereof and it extends substantially the entire distance from the proximal end 14 to the distal end 16. In FIG. 1, the channel 20 is shown as spirally traversing the body member 12, but it is to be understood that the channel or channels may be straight, as well. With no limitation intended, for a drain device having an outside dimension of 0.21 inches, the helical channel 20 may have a depth of approximately 0.06 inches. The body member is preferably fabricated from a flexible polymer material, such as silicone, silastic, polyurethane or another thermoplastic elastomer having a durometer shore hardness between about 30 and 95 shore A.

Disposed proximate the distal end of the bladder drain device is a bladder retention means 22 which comprises a curled end segment which can be straightened by the full insertion of a wire stylet (not shown) through the lumen 18. However, when the stylet is fully withdrawn following insertion of the drain assembly as shown in FIG. 1 into the urethra with the distal portion within the bladder, the memory property of the plastic comprising the distal end portion of the drainage device 10 allows the preformed distal end, bladder retention means 22, to form a loop or curl as illustrated. Those skilled in the art can appreciate that means other than a controlled memory property are available for creating the curl on the distal end of the drainage device. For example, a short wire segment having a preformed shaped can be embedded into the body of the drain to enhance the formation of the curl upon extraction of the stylet.

Attached to the proximal end of the bladder drain 10 is a fluid collection segment, indicated generally by numeral 24. The fluid collection segment 24 may be attached and detached from the body member 12 in a manner that will be described later herein. In its simplest form, the collection segment 24 comprises an elongated plastic tube having an internal lumen extending from the proximal end 14 of the drain segment 10 to an open proximal end 28 which forms the drain outlet. The collection segment 24 can accept a drainage bag or a plug not shown.

To facilitate removal of the drain, a strand such as a monofilament nylon line 25, is fixedly secured to the proximal end 14 of the body member 12 and extends beyond the proximal end 28 of the collection segment 24 and out the urethral opening in the penis. By grasping the monofilament line 25 by the loop 27 and pulling on the line, the memory property of the fixation member 22 is overcome and the drain can be readily pulled through the urethra and out the end of the penis. If desired, the line 25 may terminate short of the proximal end 28 of the collection segment 24 and in that event, an instrument having a hook on it may be passed up the lumen of the collection segment 24 to grasp a loop 29 tied in the line. By now pulling on the instrument, the body member 12 can again be removed.

Figure 2:
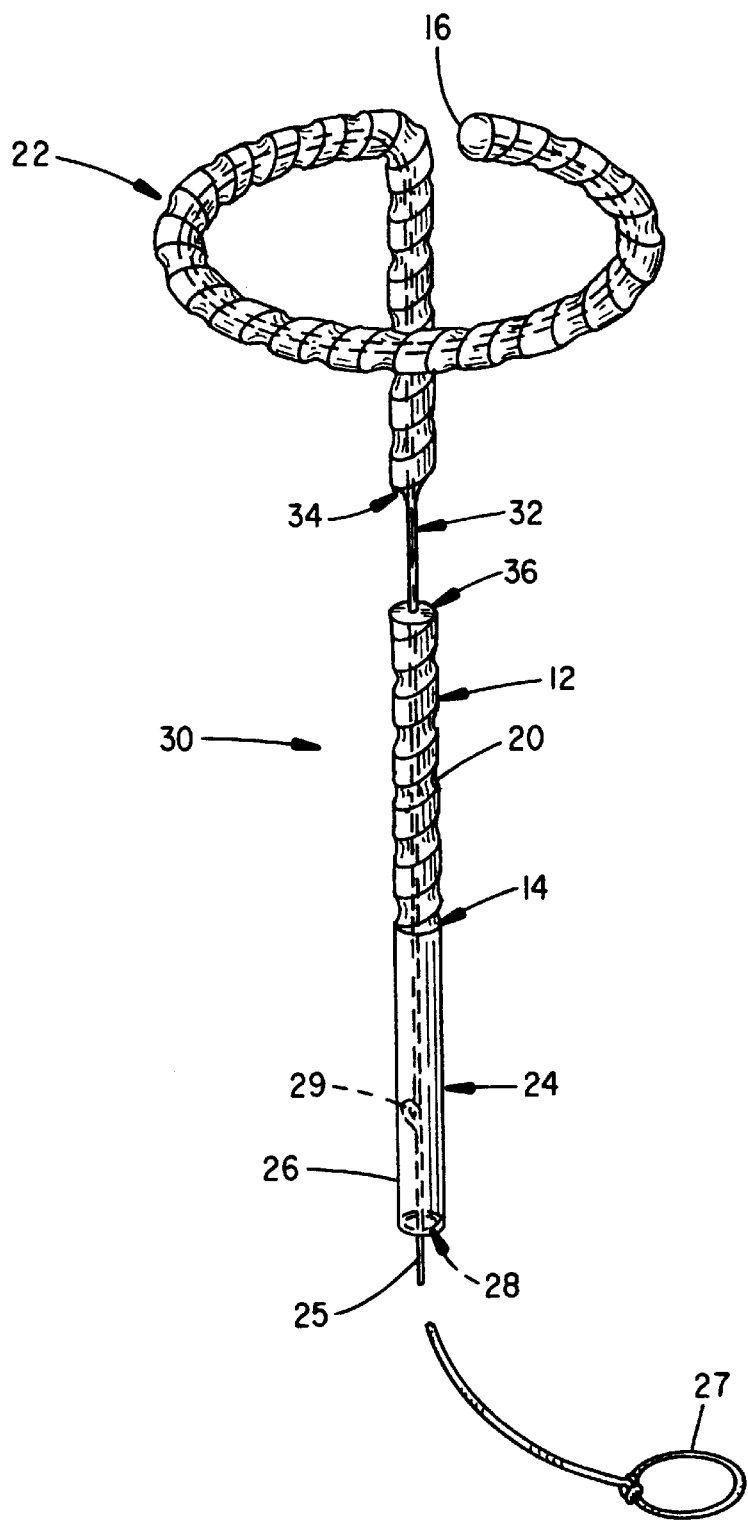
FIG. 2 is an elevational view of an alternative embodiment of the bladder drain in accordance with the invention.

An alternative embodiment of the invention is depicted in FIG. 2. The assembly of FIG. 2 is similar in most respects to the embodiment of FIG. 1 except that in the drain device 30 of FIG. 2, the tubular body member 12 includes a narrowed and smooth (non-channeled) segment 32 for cooperating with the external sphincter of the urethra. At the distal end of the segment 32 is a tapered shoulder 34 and at the proximal end is a more squared shoulder 36. The length of segment 32 is preferably in the range of from 0.5 cm to 5.0 cm and its outer diameter may be from 0.1 to 2.0 cm.

Figure 3:
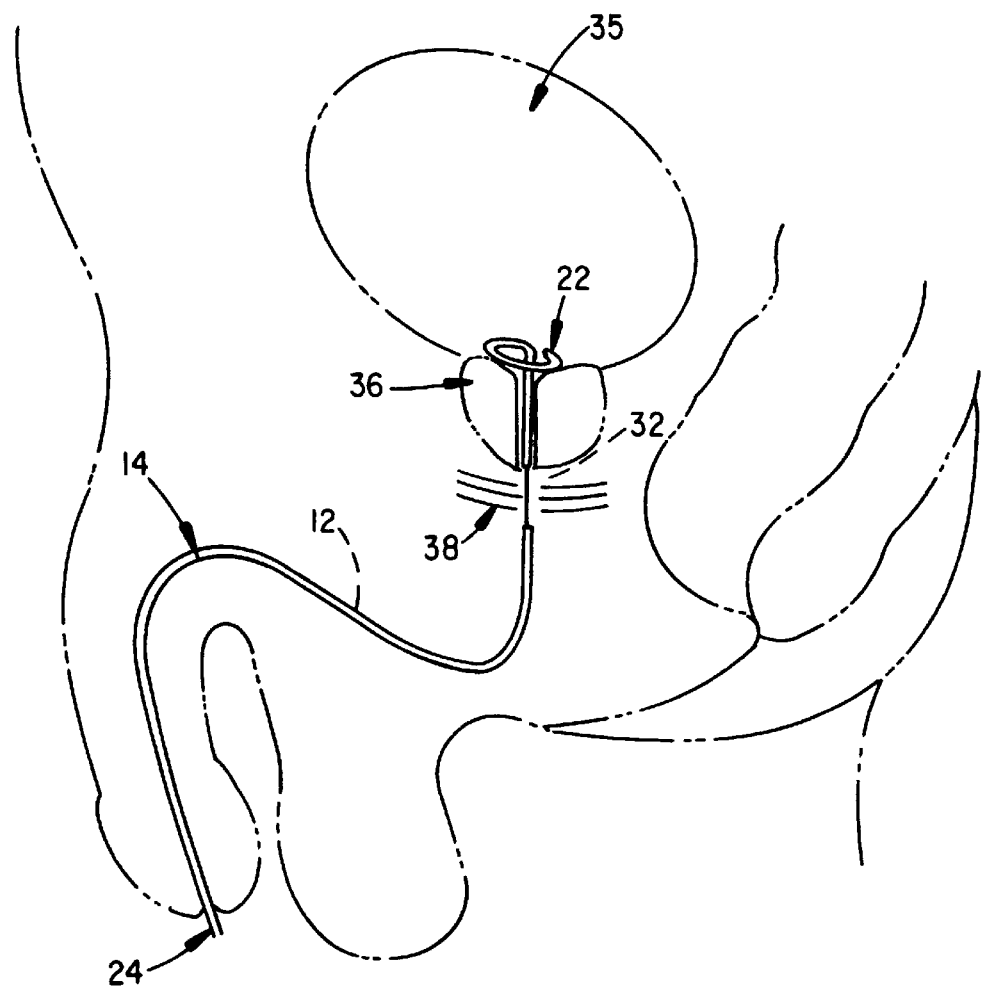
FIG. 3 is a view illustrating the embodiment of FIG. 2 inserted in the male urethra.

Referring next to FIG. 3, it shows the bladder drain device 30 of the embodiment of FIG. 2 disposed in the male urethra. The bladder retention means 22 is located proximate the neck of the bladder 35 and with the installation stylet (not shown) fully removed, the bladder retention portion assumes its flat spiral configuration, thereby holding the drainage device in place. The portion of the drainage device 30 located above the tapered shoulder 34 is dimensioned to traverse the prostate 36 and with the segment 32 of reduced diameter extending through the external urethral sphincter 38. If desired, a string or monofilament 25 can be co-extruded with the drain device of FIG. 2 to inhibit stretching of the device in segment 32 when tensile forces are applied during removal of the drain.

The spiral curl 22 comprising the bladder retention means is essentially perpendicular to the axial length of the drain and does not protrude appreciably above the base of the bladder. This low, flat profile distinguishes the present invention from the common Foley catheter, which is retained by means of a liquid filled balloon, as well as from the device shown in U.S. Pat. No. 4,738,667 to Galloway. The removal of a straightening stylet, as compared to the removal of an outer shield in the Galloway device, serves to minimize any irritation to the urethral wall of the patient. The use an internal straightening wire, as contrasted to a design utilizing an external straightening sleeve, also allows the existence of deeper drainage channels for a given outer diameter of the drain itself. While the bladder retention segment is depicted as a spiral or curl at the distal end of the body member 12 comprising the drain, it can be appreciated that an inflatable balloon adhered to the exterior of the tubular body member 12 and communicating through a port bridged by the balloon leading to an inflation lumen may be employed to anchor the drain in a fashion similar to what is conventionally used with a Foley catheter. Such an arrangement is shown in FIG. 1(a), with the silastic balloon identified by numeral 39.

With the embodiment of FIG. 2 in place, as illustrated in FIG. 3, there will be a continuous flow of urine from the bladder 35 through the channel 20 formed in the exterior wall of the drain segment 30 with the channel emptying into the lumen of the urine collection tube 26. For patients having a functioning external urethral sphincter 38, the compressional force on the urethra in the zone 32 of the drain will close the urethra against that segment thereby blocking urine flow. When the patient desires to drain his or her bladder, he or she voluntarily relaxes the external urethral sphincter 38, allowing the contents of the bladder 35 to flow through the channel(s) formed in the wall surface of the drainage device 30 to again empty into the urine collection tube 26 leading to a collection bag (not shown).

Figure 4:
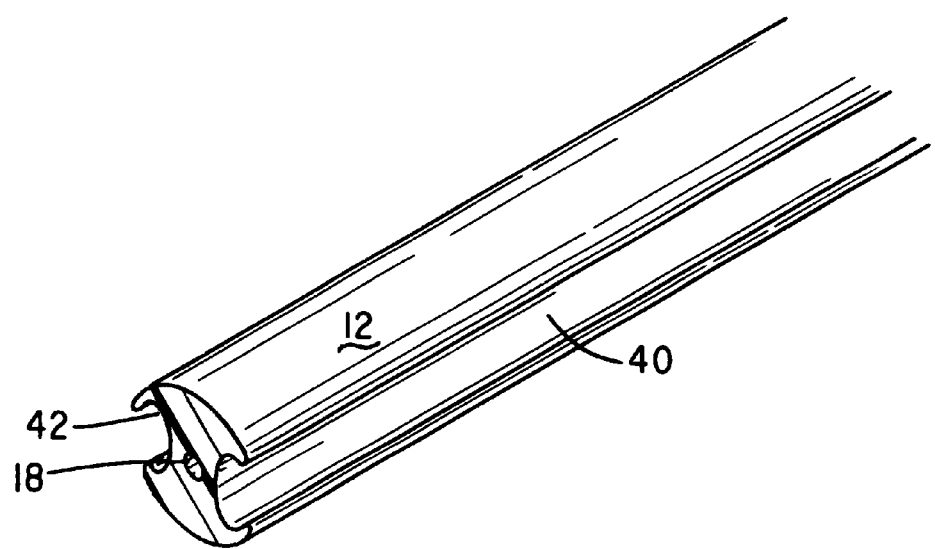
FIG. 4 is a fragmentary, enlarged perspective view of the portion of a bladder drain, illustrating two straight surface grooves.
Figure 5:
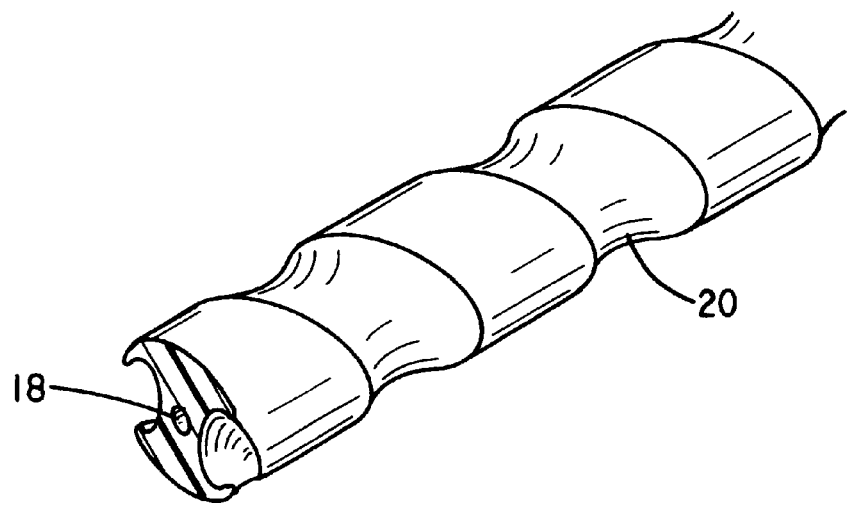
FIG. 5 is a fragmentary, enlarged perspective view of a portion of a bladder drain illustrating spiral surface grooves.

FIGS. 4 through 7 are included to show alternative ways of configuring the drainage segments 10 and 30 illustrated in FIGS. 1 and 2, respectively. In FIG. 4, the body member 12 includes two straight longitudinal channels 40 and 42, diametrically opposed from one another, that extend substantially the entire length of the body member. Also visible in FIGS. 4 through 7 is the stylet lumen 18. In the embodiment of FIG. 5, the surface grooves or channels, as at 20, form a spiral, as in the embodiments of FIGS. 1 and 2. This spiral pattern may conveniently be formed during the fabrication process by twisting the body member 12 during the extrusion process prior to cooling. By controlling the amount of twisting, the pitch of the channels can be controlled.

While linear channels of the type shown in FIG. 4 may be provided in the drainage segment, a spiral channel configuration is preferred in that the lateral projections on the outer surface of the drain will interact with the urethral wall in such a fashion as to retard movement of the drain along the axial length of the urethra, thus minimizing undesired migration thereof. The side walls of the channels are preferably undercut or dished, as at 44 (FIG. 6), to thereby prevent irritation of the urethra, and to inhibit invagination of the urethral wall tissue into the channels.

Figure 6:
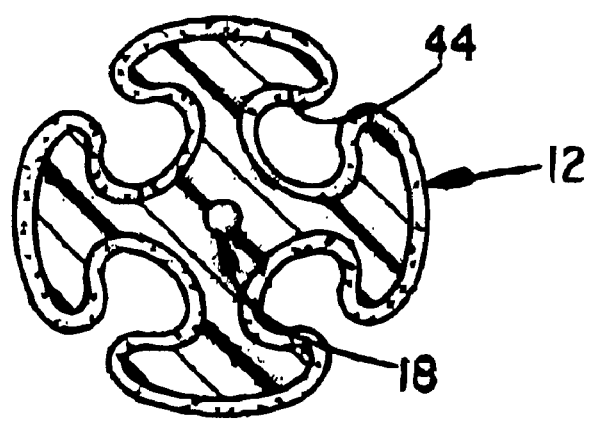
FIG. 6 is an enlarged cross-sectional view of a portion of the body of a bladder drain having four surface grooves extending the length thereof.
Figure 7:
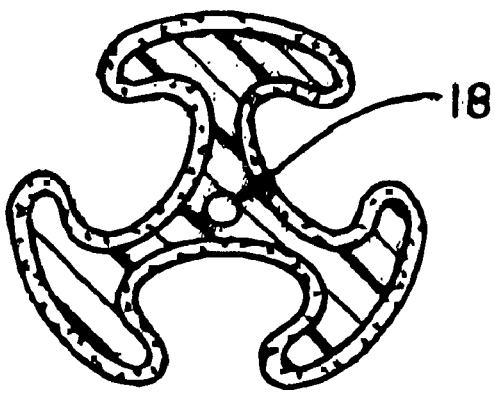
FIG. 7 is an enlarged cross-sectional view through a portion of the body of a bladder drain having three surface grooves extending along the length dimension thereof.

FIGS. 6 and 7, respectively, show cross-sectional views of the drain in which four and three channels, respectively, extend the length thereof.

Figure 8:
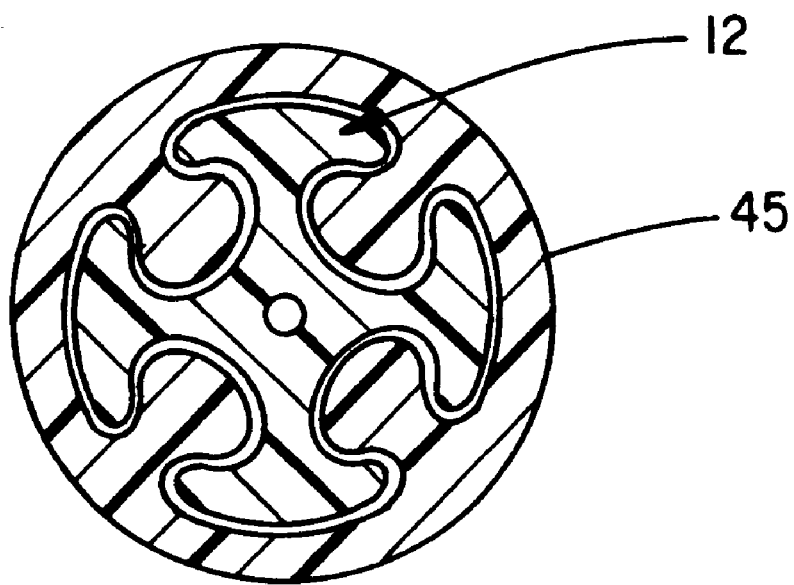
FIG. 8 is an enlarged cross-sectional view through a portion of the body of a bladder drain having a positionable smooth sleeve segment affixed thereto.

Referring to the cross-sectional view of FIG. 8, another way of forming a smooth segment along the length of the body member 12 for cooperating with the external urinary sphincter of a given patient is to provide a short length of tubing, as at 45, having an internal lumen whose side walls are complimentary in shape to the exterior surface of the grooved body member 12. Thus, the smooth portion of the tube 45 can be longitudinally adjusted to a location along the drain body where the urinary sphincter is located for that patient. Also, the outside diameter of the removable and replaceable smooth tubular segment 45 can be selected to accommodate the particular contractibility of the urinary sphincter of the patient to provide increased continence and will usually be in the range of from 0.3 cm to 1.0 cm.

Figure 9:
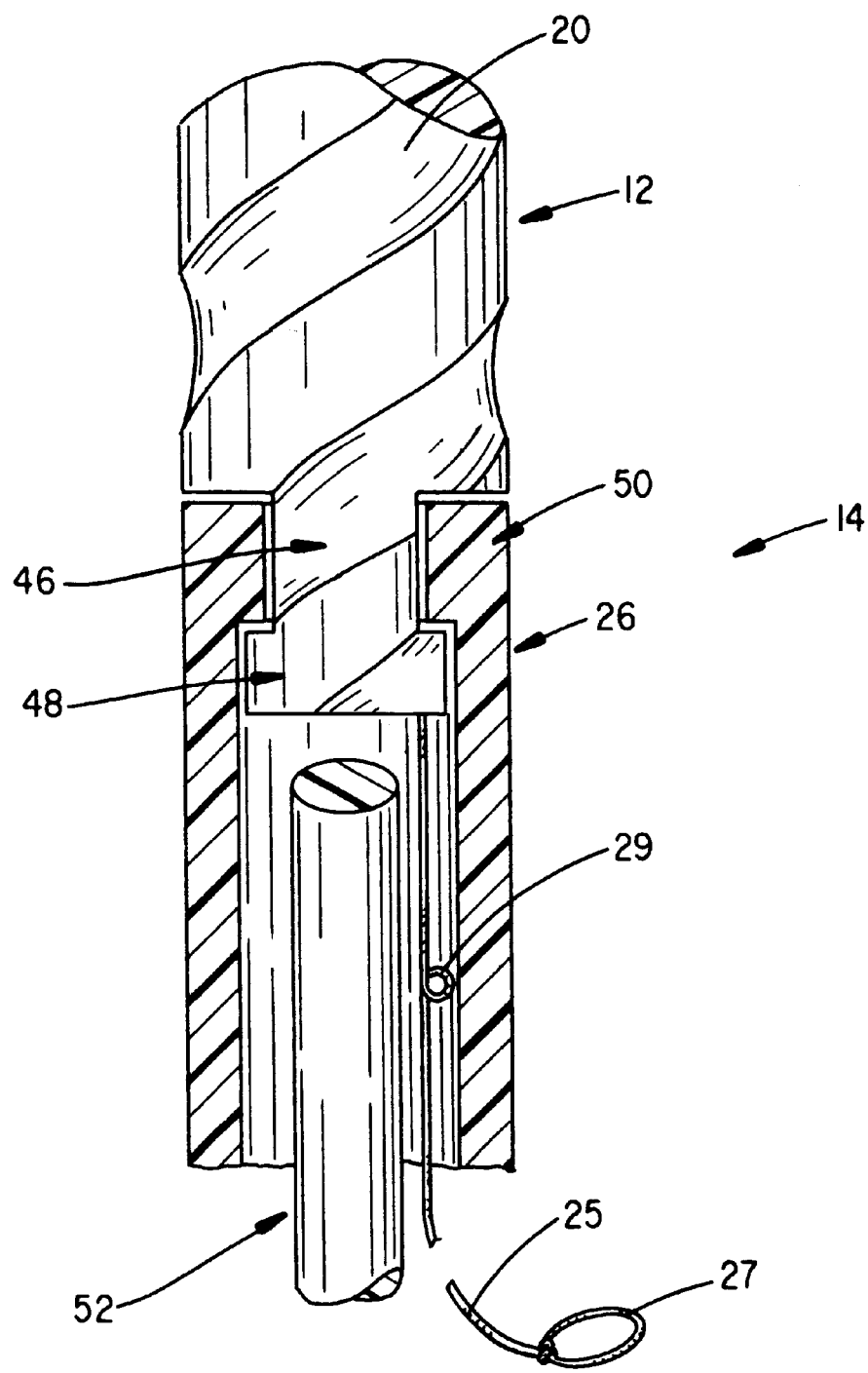
FIG. 9 is a partially sectional, fragmentary view of the embodiment of FIG. 1 or 2 proximate the junction between the grooved bladder drain element and its associated collection segment.
Figure 9:
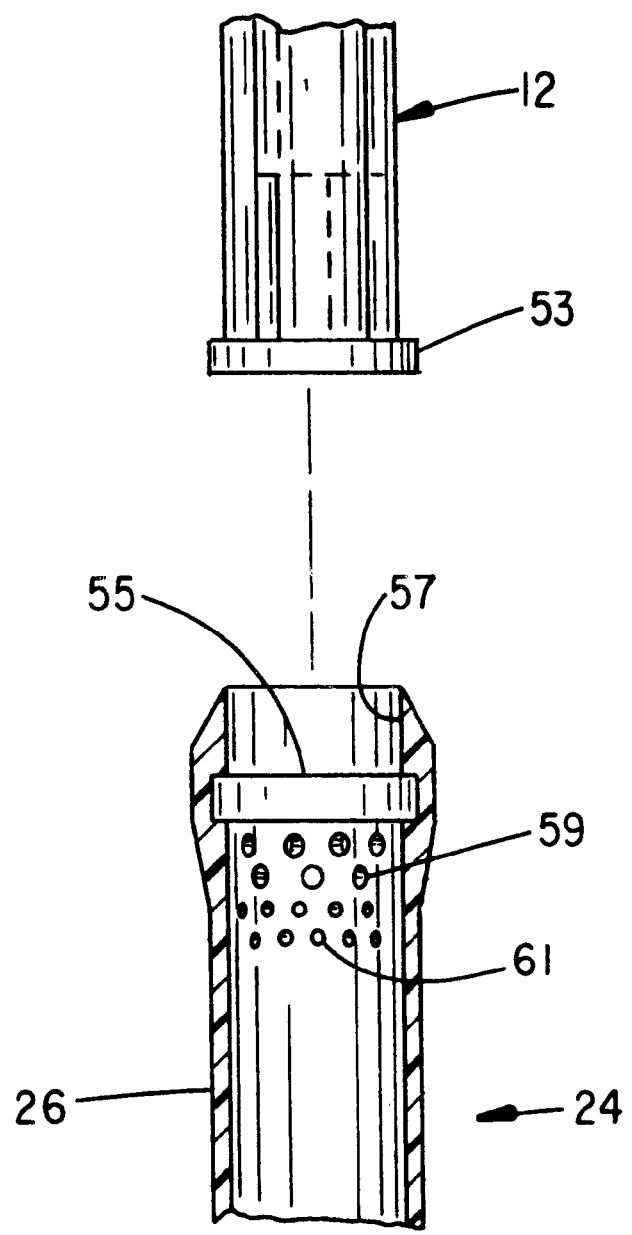

It is further contemplated that the smooth tubular member 45 on the female urethral drain can comprise an inflatable sleeve surrounding the body member 12 (FIG. 9). This is deemed to be beneficial in cases of female stress incontinence in that the sleeve can be inflated after placement to a degree effective to preclude leakage between the expandable sleeve and the neck of the bladder and to compensate for sphincter deficiency.

Referring now to FIG. 9, there is shown an enlarged fragmentary, partially sectioned view of the bladder drain showing the manner in which the fluid collection tube 26 is joined to the proximal end of the grooved body member 12. The proximal end 14 of the body member 12 is provided with a narrowed neck 46 which is followed by an expanded end portion 48. The fluid collection tube 26 has a complimentary profile 50 adapted to snap over the end portion 48 to occupy the narrowed neck 46. Urine passing along the channels 20 between the internal wall of the urethra and the drain is channeled into the lumen of the collection tube 26 to flow out its proximal end 28, either continuously when the embodiment of FIG. 1 is employed or in a controlled manner when the embodiment of FIG. 2 or 8 is utilized. Detachment of the flexible plastic collection tube 26 may be accomplished by pulling on the tube 26 in the proximal direction while simultaneously employing a stabilizing push rod 52 to hold the body member 12 in place. After detachment of the collection tube 26, the drain device is entirely contained within the urethral tract.

FIG. 9(a) is an enlarged, exploded, partial sectional view of a body member 12 having straight (non-spiral) grooves such as is illustrated in FIG. 7 of the drawings and illustrating an alternative arrangement for connecting the drain body member to an associated collection tube. The drain body member 12 is molded or extruded so as to have a plurality of straight parallel grooves as best seen in FIG. 7. Surrounding the proximal end portion of the drain body member 12 is a ring member 53 which is secured to the exterior of the lobes of the drain body separated from one another by adjacent grooves. To better concentrate and direct the urine stream, the central portion of the drain body is cored out, leaving only the lobes depending in a zone of a predetermined length distal of the ring 53. The collection tube 26 includes an internal annular groove 55 into which the ring 53 on the drain body member is adapted to be inserted. As such, the portion of the lobes on the drain body member that are free from the central or core portion thereof fall within the lumen 57 of the collection tube and thereby directing the urine stream flowing down the longitudinal grooves in the drain body to flow into the lumen 57 of the collection tube.

To enhance the ability of the urine to find its way into the central lumen of the collection tube, it may be expedient to include a pattern of holes as at 59 through the wall of the collection tube where the size of the holes 59 are made slightly larger toward the distal end of the collection tube 26 and of a smaller size as at 61 at locations more proximal than the larger holes.

As those skilled in the art will appreciate from the foregoing description of the embodiment of FIG. 9, the same technique for detaching the plastic collection tube 26 from the body member 12 can be utilized with the embodiment of FIG. 9(a).

Figure 10:
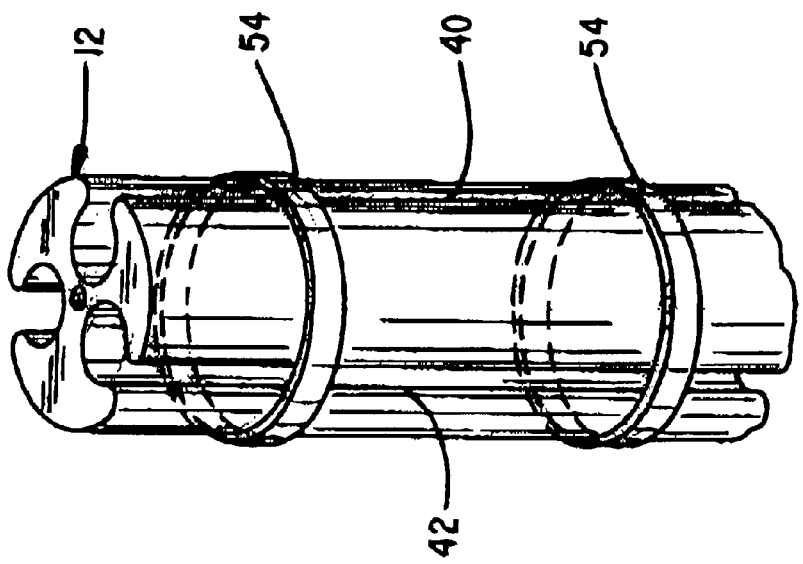
FIG. 10 is an enlarged, partial, perspective view of a segment of the drain of FIG. 7 and incorporating retention rings thereon.

As a means for inhibiting longitudinal migration of the drain devices having linear channels as in FIGS. 4 through 7, a series of longitudinally spaced rings as at 54 in FIG. 10, may be placed about the drain body member 12 at predetermined intervals. The rings are preferably relatively flat and are appropriately bonded to the body member 12. It is found that the tissue of the inner wall of the urethra invaginates the channels 40, 42 on opposite sides of the rings 54, inhibiting longitudinal displacement of the drain assembly. With no limitation intended, the rings 54 may be approximately 2 mm wide and 1 mm thick. Further, they may be placed approximately 1 cm apart from one another along the length of the drain body 12 on one or both sides of any smooth segment of reduced diameter as at 32 in FIG. 2 that is intended to cooperate with the urinary sphincter. By providing rings 54 along the length of the drain device, it is no longer necessary to include a central stylet receiving lumen 18. The stylet, instead, can be routed up one of the surface channels 40 and 42 and will be constrained by the rings.

Figure 11:
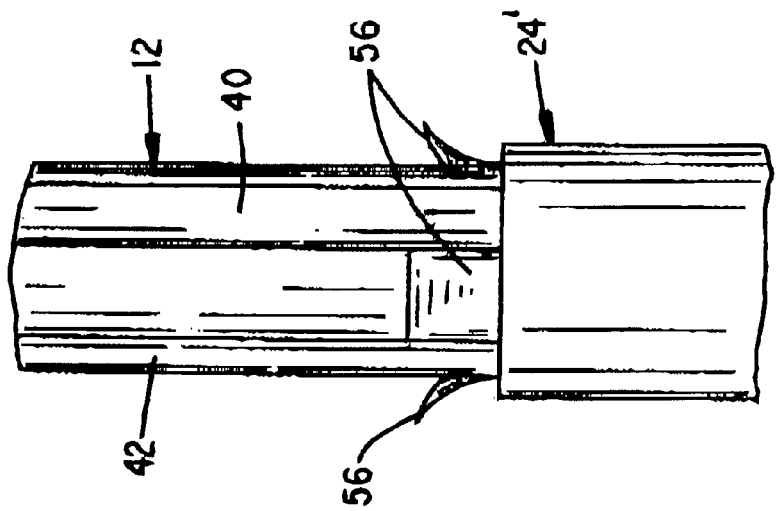
FIG. 11 is a partial side elevation of a drain device having the configuration of FIG. 7 and illustrating an alternative drain retention feature.

FIG. 11 shows an alternative anchoring arrangement to that shown in FIG. 10. Instead of incorporating spaced-apart rings extending about the drain body member, small, laterally projecting tines 56 that are located proximate the junction between the body member 12 and the collection segment 24'. The tines 56 are intended to engage the interior wall of the urethra to prevent migration of the drain assembly in the distal direction toward the urinary bladder. When it is desired to remove the drain, a force applied to the strand 25 (FIG. 1) will cause the tines 56 to deflect or collapse into alignment with the wall of the tubular body member 12 and offer practically no drag or resistance against movement in the proximal direction. While the tines 56 are shown as being formed by cutting or slicing into the elastomeric material comprising the drain body member 12, such tines can alternatively be provided on the collection segment 24'. Furthermore, rather than providing tines as at 56 in FIG. 11, the retention means can take the form of a bulbous protrusion (not shown) formed on the lobes of the drain body member 12.

Figure 12A:
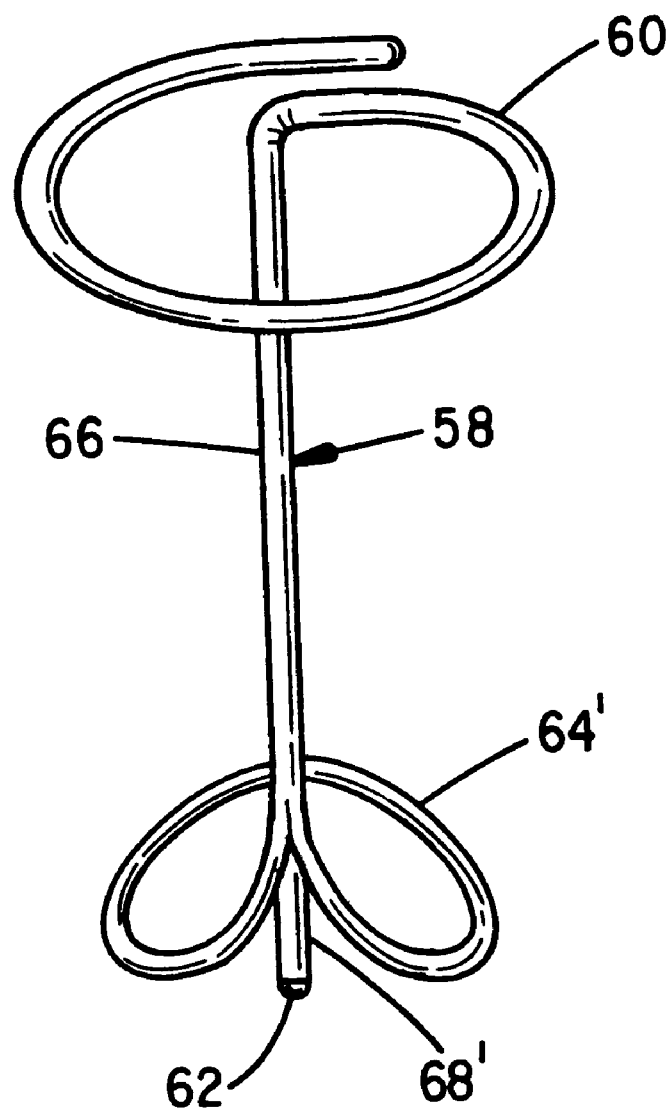
FIG. 12 illustrates an alternative embodiment of the invention for placement in the female urethra.
Figure 14:
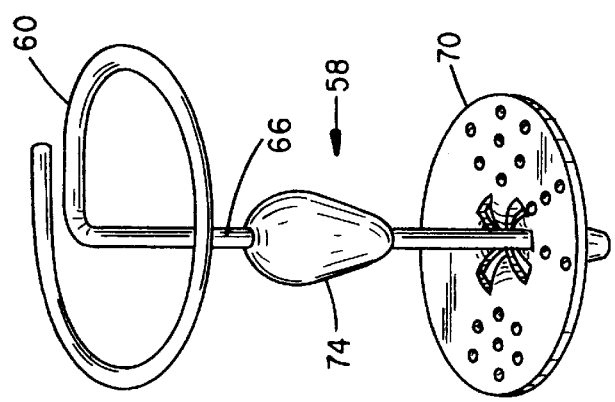
FIG. 14 illustrates the device of FIG. 12 or 13 with a cuff member placed thereon when treating female stress incontinence.
Figure 13:
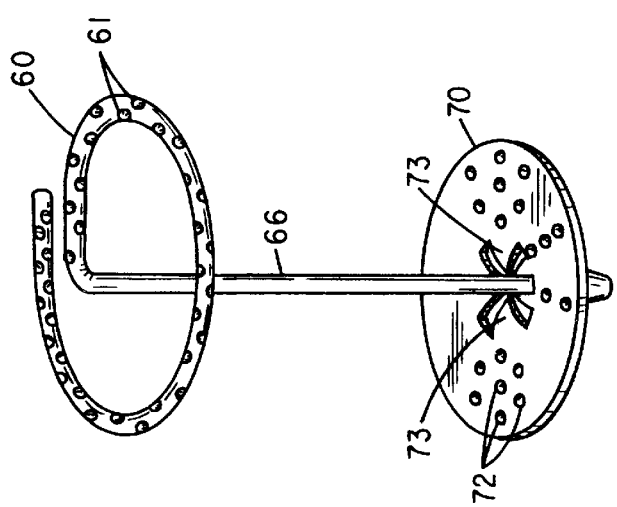
FIG. 13 illustrates the device of FIG. 12 but with an alternatively configured proximal retention means.
Figure 12:
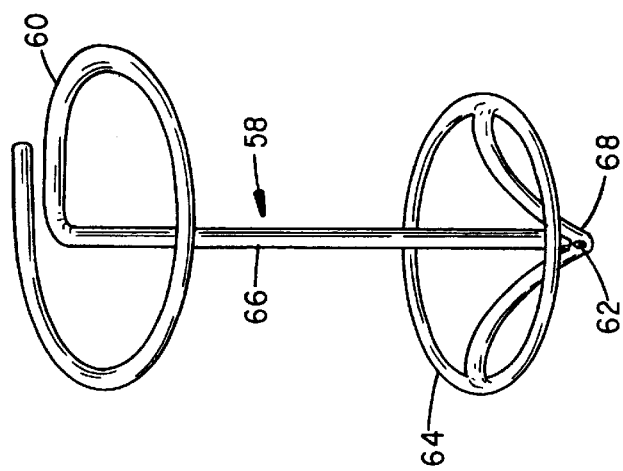

FIGS. 12, 13 and 14 show the configuration of alternative devices insertable into the female urethra for addressing stress incontinence. It is seen to comprise an elongated, flexible, plastic rod which, in the instant embodiments, is free from surface channels throughout its length. Preformed at its upper end is a retention segment 60 which is intended for placement within the urinary bladder. Such placement is enhanced by inserting a suitable stylet through an aperture 62 for temporarily straightening the curl of the retention segment 60 and allowing its insertion into the urethral opening. When the device 58 has been advanced sufficiently far up the urethra such that the segment of the device forming the retention member 60 resides in the urinary bladder, upon removal of the stylet, the memory property of the plastic material comprising the device 58 allows the retention member to reform into a flat spiral shape as illustrated.

To prevent the upward migration of the device as it is being worn, it is also provided with a proximal retention segment 64 which, in FIG. 12, also comprises a flat ring-like segment that lies in a plane that is at a predetermined angle to the body portion 66 of the drain member and that is dimensioned to abut the vestibule and underlie the labia minora. As such, the device may remain within the patient while still allowing normal sexual activity to take place.

Instead of forming the proximal end portion of the body portion 66 into a flat spiral such as is shown at 60 in FIG. 12, to create a retention member, it is also contemplated that a separate closed ring as at 64 positioned about the drain body portion and secured to it by connecting spokes made from a suitable soft plastic be used. This is the configuration illustrated in FIG. 12.

It has been found expedient to preform the device 58 so that the elongated straight segment comprising body portion 66 extends downward below the lower retention member 64 as indicated by numeral 68 in FIG. 12. Urine flow tends to follow the straight portion 66 due to surface tension effects and provides a proper urine stream leaving the urethra. In some patients, the projecting portion may cause irritation and become a source of discomfort. The proximal end 68 of the drain member body portion 66 may also be located above the plane of the ring-like proximal retention segment 64 and, therefore, remain fully within the urethra, but close to the meatus. The segment 64, however, remains in the vestibule covering areas anterior, lateral and posterior to the meatus.

The embodiment of FIG. 13 is like that of FIGS. 12 and 12(a) except that the proximal retention ring 64 is replaced by a highly flexible oval-shaped sheet of plastic 70 that is permeable to the flow of air, due to the fenestrated nature of the plastic material shown as a having a pattern of closely spaced openings, as at 72, extending through the thickness dimension thereof. Again, the air pervious retention member disk 70 is sized and shaped to conform to the area of the body closely surrounding the urethral opening in the vestibule. The proximal end of the body portion 66 extends below the retention member 70 and is supported by webs, as at 73, extending across a larger circular opening formed in the sheet 70 which permits urine to flow in a stream as it exits the device.

In the embodiment of FIG. 13, measures are taken to decrease the weight of the retention member 60. Here, the curl portion only is made tubular and is fenestrated by a plurality of openings 61 extending through the wall of the curl to the lumen thereof. This minimizes trauma to the bladder.

Referring next to FIG. 14, the incontinence control device 58 may include an appropriately sized cuff member 74 placed on and affixed to the straight body portion 66 of the device of FIGS. 12 and 13 at a location that will conform to the shape of the urethra proximate the woman's urinary sphincter. A urologist, fitting the woman with the device, will determine the appropriate size and shape of the cuff member 74 that will cooperate with the sphincter muscle to provide an effective seal when the sphincter is contracted. The cuff 74 may include a longitudinal bore sized so that the plastic body portion 66 comprising the device and its retention member 60 can pass through that bore. Alternatively, the cuff member 74 may be provided with a fine slit extending through a side wall surface thereof to a central bore, allowing it to be assembled onto the device 58 by first spreading the cuff member and fitting it over the straight segment comprising body portion 66. Releasing the cuff member allows it to close about the straight portion.

FIGS. 15A, B and C illustrate alternative shapes for the cuff member 74 from which the urologist may choose in deciding which provides the best seal with the urethra when the urinary sphincter is contracted. The cuff of FIG. 15A is generally cylindrical but has conically tapered opposed ends to facilitate its being inserted and removed from the urethra along with the device 58. FIG. 15B is somewhat bone-shaped where the sphincter cooperates primarily with the narrowed zone between the two larger opposed end portions. The cuff of FIG. 15C has multiple annular narrowed regions which can assist deficient sphincter muscles to better coapt the urethral wall to the cuff during a sudden increase in bladder pressure occasioned by laughter, coughing or sneezing.

ALTERNATIVE EMBODIMENT

Figure 16:
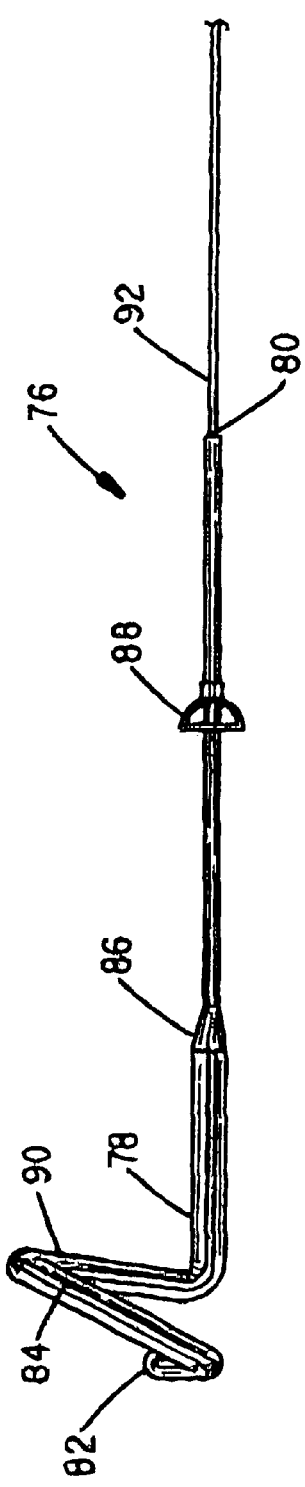
FIG. 16 illustrates an alternative preferred embodiment of a bladder drain in accordance with the invention.

Referring to FIG. 16, there is indicated generally by numeral 76 a urinary drain comprising an alternative embodiment to the present invention. It is seen to comprise an elongated, flexible tubular body member 78 having a proximal end 80 and a distal end 82 with a stylet receiving lumen (not shown) extending from the proximal end 80 toward but just short of the distal end 82. Thus, the distal end 82 covers the stylet lumen, precluding the flow of body fluids therethrough when the drainage device 76 is appropriately placed within the urinary tract of the patient.

The body member 78 of the drainage device 76 is shown as including at least one channel 84 formed in the surface thereof and it extends from the distal end 82 to a zone 86 where the outside diameter of the drain body member 78 tapers to a lesser diameter where the drain body is void of any surface groove. As with the embodiment of FIG. 1, the drain body member 78 may have an outside dimension of about 0.21 inches in the portion distal of the tapered zone 86 and the channel 84 formed in this portion may have a depth of approximately 0.06 inches. Again, the body member 78 is preferably fabricated from a flexible polymer material, such as silicone, silastic, polyurethane or another thermoplastic elastomer having a durometer between about 30 and 95 Shore A.

Affixed to the drain body member 78 at a location that is a predetermined distance proximal of the tapered zone 86 is an anti-migration cage 88. This cage, shown in enlarged form in FIG. 20 comprises a means for inhibiting longitudinal migration. It is designed to cooperate with the internal wall of the urethra at a location proximal of the patient's urinary sphincter to prevent distal migration of the drain body within the urinary tract of the patient in whom it is placed.

Disposed at the distal end of the bladder drain device 76 is a bladder retention segment 90 in the form of a curled distal end portion which is adapted to be straightened at the time of insertion into a patient by the advancement of a stylet device within the aforementioned stylet receiving lumen. The details of this process will be considered in greater detail below with the aid of FIGS. 17–19.

Affixed to the proximal end 80 of the drain body 78 is an elongated string or thread 92. The string or thread 92 may be of a length sufficient to extend from its connection point at the proximal end 80 of the drain body or beneath the cage 88 out and beyond the urethral meatus.

Figure 17:
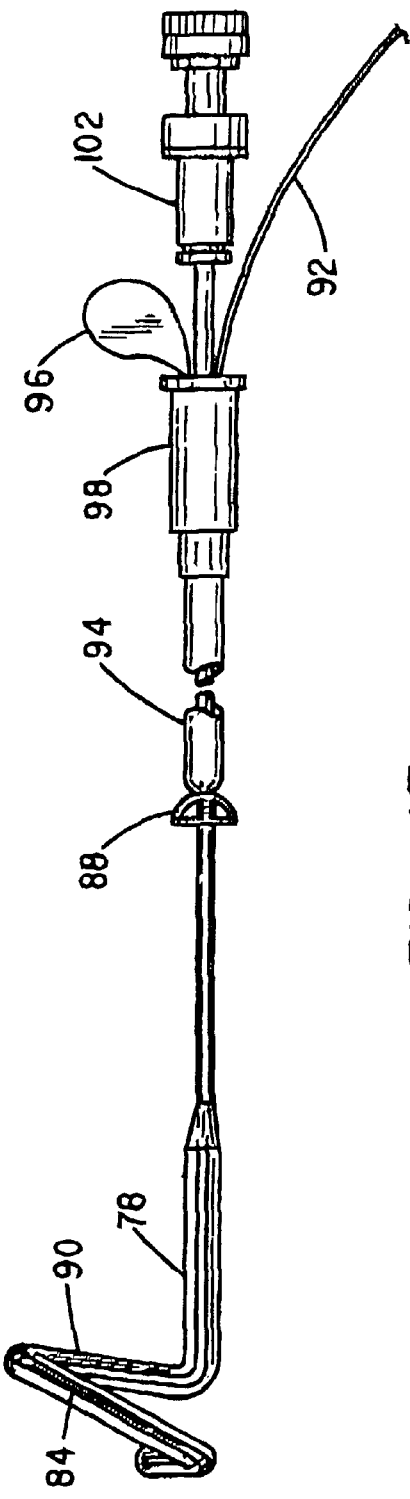
FIG. 17 shows the bladder drain of FIG. 16 as it is packaged for use by a medical professional.

FIG. 17 illustrates the flexible, self-cleaning urethral drain and its associated deployment device and stiffening stylet as it is packaged by the manufacturer prior to use. The drain 78 has the thread or string 92 affixed to it and extending through a central lumen of a pusher member 94. A rigid clip 96 is secured to the string by a knot in the string 92 such that when the thread 92 is taut, the clip 96 engages the molded plastic hub 98 affixed to the proximal end of the pusher 94. With the anti-migration cage 88 being of a larger diameter than the diameter of the central lumen of the pusher 94, the anti-migration cage 88 will be held in place against the distal end of the pusher 94. The molded hub 98 on the proximal end of the pusher member 94 allows it to be readily gripped during use.

Figure 19:
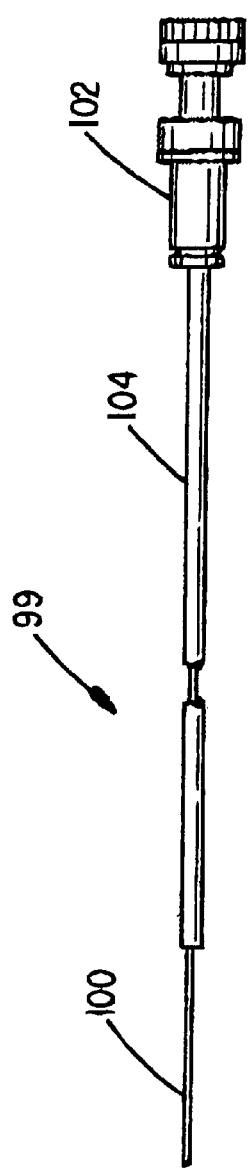
FIG. 19 illustrates the straightener of FIG. 18 removed form the drain and collection tube.

Referring momentarily to FIG. 19, the stiffening stylet 99 used with the alternative embodiment is seen to comprise a fine semi-rigid wire 100 whose overall length is sufficient to extend through the tubular drain body 78 when the hub/handle 102 affixed to the proximal end of the wire 100 is made to abut the proximal end of the hub 98 of the pusher member 94. Surrounding the wire 100 and extending toward the proximal end 80 of the drain body when contained within the pusher member 94 is a plastic tubular sheath 104.

Referring again to FIG. 17, when in the package prior to use, the stiffener or stylet 99 of FIG. 19 is partially retracted with its hub 102 spaced a distance back proximally from the proximal end of the molded plastic hub 98 on the pusher member. As such, the wire 100 does not extend into the curled bladder retention portion 90, so that the curl forms at the distal end of the drain body.

The stiffening device 99 of FIG. 19 is partially retracted during shipping and storage so that plastic deformation does not result in a permanent loss of the ability of the drain member to revert to a curl in the bladder following insertion of the drain into the patient's urethra after the stiffening member 99 is removed.

Figure 18:
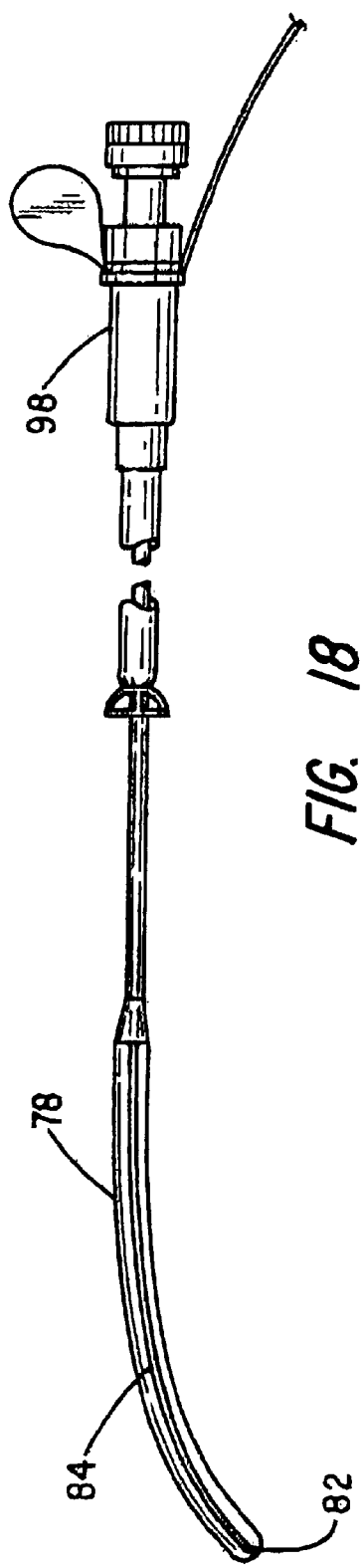
FIG. 18 shows the drain of FIG. 17 with its straightener deployed.

In FIG. 18, the stiffening member of FIG. 19 is shown as being fully advanced so that the hub 102 thereof abuts the molded plastic hub 98 on the proximal end of the pusher 94. With the stiffening device 99 fully inserted, the wire 100 is effective to straighten the curl of the bladder retention portion 90 such that the distal end 82 of the drain device can more readily be inserted into the patient's urethra. Once the distal end portion of the drain body has been advanced into the urinary bladder and the stiffening device completely withdrawn, the memory property of the plastic comprising the drain body will result in the return of the curl formation on the drain body to provide bladder retention.

The insertion procedure takes place by grasping the hub 98 on the pusher member 94 while simultaneously advancing the stylet 99 until the stylet wire advances through the stylet lumen of the drain body 78 to the point where the distal curl is straightened. The clip 96 abutting the hub 98 prevents separation of the drain body from the pusher member, because, as illustrated, the clip is of a larger size than the diameter of the lumen of the pusher member 94. The distal tip of the drain body is then positioned at the meatus and advanced through the urethra by simultaneously advancing both the stylet 99 and the pusher member 94 through the urethra until the distal end portion of the drain body is positioned in the bladder. While continuing to grip the hub 98 of the pusher member to prevent movement of the drain body in the proximal direction, the stylet 99 is pulled free of the assembly, allowing the distal end portion of the drain body to reassume its curled condition for retaining the drain body in the bladder and urethra. Next, the clip 96 can be removed from the string or tether 92 allowing the pusher member 94 to be stripped free of the drain.

When it is desired to remove the drain device, the string 92 may be grasped and tensioned resulting in the curl 90 being drawn through the bladder neck and straightened as it is pulled down through the urethra.

Figure 20:
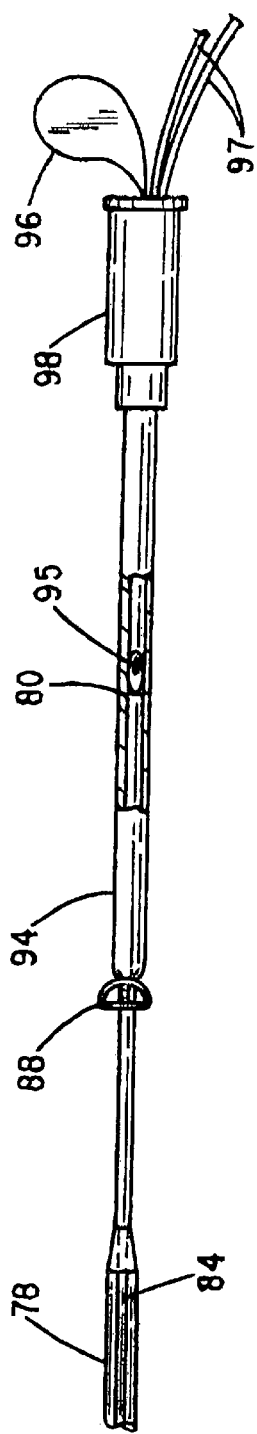
FIG. 20 shows an alternative tether for the bladder drain device.

The foregoing description of the removal of the drain removal procedure contemplates that the string or tether 92 will extend out through the meatus. With some patients, the presence of the string hanging from the end of the penis may not be acceptable. FIG. 20 illustrates a way in which the tether may be configured so that upon insertion of the drain into the patient's urethra, the portion extending beyond the meatus may be readily removed. In the arrangement of FIG. 20, instead of having a single strand 92 connected to the proximal end portion 80 of the drain body, a small closed loop of string 95 comprising a first separable segment is secured to the drain body and longer string segment 97 engages the loop 95 and extends out beyond the distal end of the hub 98 where its ends can be tied to form a larger loop. Once the drain is inserted into the urethra in the manner described above, when the clip 96 is removed from the strands, the pusher 94 can be stripped out of the urethra and by cutting the loop 97, it can be pulled free of the loop 95, with loop 95 remaining totally within the urethra. A thin wire stylet having an atraumatic hook-shaped tip may be inserted through the meatus and up the urethra to engage the loop 95 when it is desired that the drain be withdrawn from the body.

Figure 21:
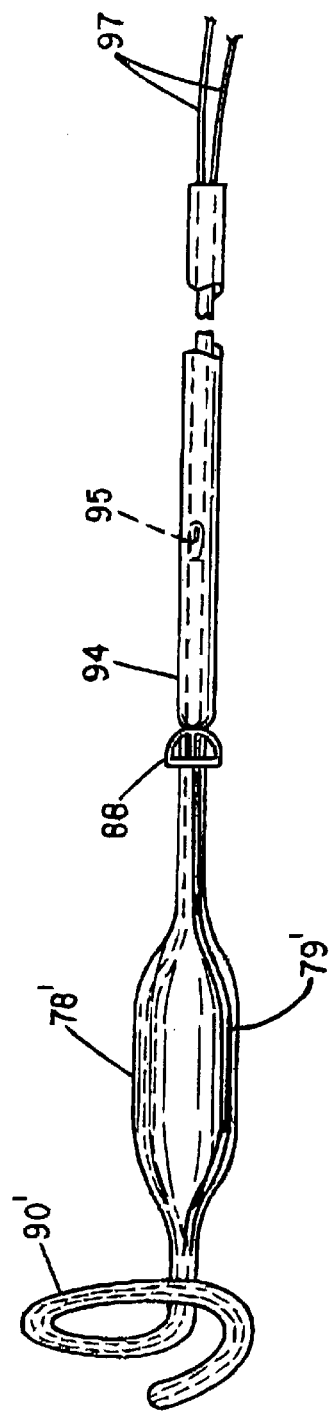
FIG. 21 shows a further embodiment of a urethral drain having an enlarged drain segment for cooperating with the prostate.

In the embodiments of FIGS. 1 and 2 and FIGS. 16–20, the bladder retention curl 22,90 is shown as being of the same diameter as the portion of the drain body that cooperates with the male prostate gland. It has been experimentally determined that for a given Shore A hardness, e.g., 70, a bladder retention portion diameter of 17 Fr is about the maximum size that a patient can tolerate easily. Larger diameter bladder retention segments create too high of a bladder retention strength, resulting in discomfort when the catheters are being removed. There are incidences, however, where additional urine flow is desired through the portion of the urethra subtended by the prostate. The urinary drain configuration shown in FIG. 21 is designed to allow such increased urine flow past the prostate gland. In this arrangement, the bladder retention curl 90' is designed to be of a lesser diameter than the portion 78' that is designed to span the prostate gland. Thus, for example, the bladder retention portion 90' may have a diameter of about 16 Fr while the portion 78' may have a diameter of about 24 Fr, allowing for deeper grooves 79' for urine to flow through.

Figure 22:
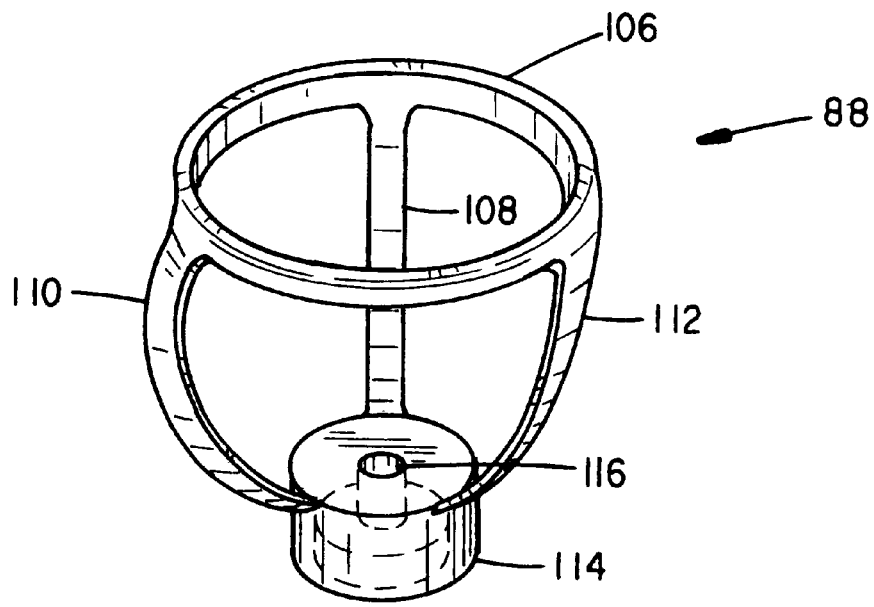
FIG. 22 is a greatly enlarged view of the anti-migration device used with the bladder drain of FIG. 16.

FIG. 22 is a greatly enlarged view of the anti-migration cage 88 used with the drain device 76 of FIG. 16. It is seen to comprise a flat ring 106 that is supported by a plurality of integrally formed ribs 108, 110 and 112 that are arcuately formed and joined to a tubular base 114 to form a cage-like structure. The reduced diameter portion of the drain body 78 proximal to the tapered section 86 fits through a bore 116 formed in the base 114 and is bonded in place at a location that will be proximal of the patient's urinary sphincter when the retention curl is disposed in the urinary bladder and the portion of the drain body distal of the tapered section 86 spans the patient's prostate gland. The flat distal end of the annulus ring 106 engages the inside wall of the urethra and abuts the closed external sphincter muscle to inhibit longitudinal migration thereof in the distal direction while still permitting urine to flow through the open cage-like structure once voluntary voiding takes place as the patient relaxes his urinary sphincter. Because the arcuate ribs 108, 110 and 112 are deformable and because the tubular base 114 is of a significantly smaller diameter than the annulus ring 106, removal of the drain from the urethra does not result in damage to the delicate lining thereof as the string 92 is pulled on to displace the drain.

Figure 23:
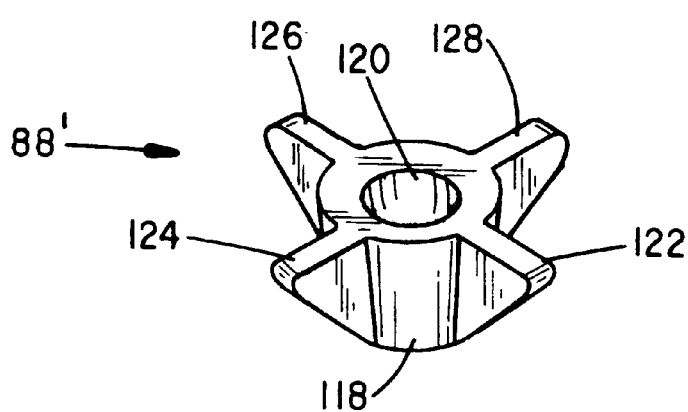
FIG. 23 shows the configuration of an alternative anti-migration device.

FIG. 23 shows an alternative construction of an anti-migration cage 88' that can be used on the urinary drain of FIG. 16. It comprises a tubular body 118 having a central bore 120 for receiving a portion of the drain body therethrough. The anti-migration cage 88' of FIG. 21 is also bonded to the drain body at the appropriate location there along. The tubular body 118 includes a plurality of integrally formed, regularly circumferentially-spaced, rounded and tapered lobes 122, 124, 126 and 128. The lobes cooperate with the urethral wall proximal of the urinary sphincter when the drain is in place. The lobes serve to hold the urethral wall in spaced relation to the remainder of the tubular body so as to allow for urine flow therebetween. As with the anti-migration cage 88 of the FIG. 21, the tapering shape of the cage 88' of FIG. 22 facilitates subsequent removal of the drain from the urethra while the upper edge surface thereof (when viewed as in FIG. 22) as well as the radially projecting lobes function to inhibit unwanted movement of the drain device in the distal direction following the insertion thereof into the urinary tract.

The anti-migration cages 88 and 88' described herein are considered an improvement over prior art balloon anti-migration structures which require complex inflation and deflation mechanisms and which are subject to mechanical failures. More importantly, prior art balloon anti-migration devices occlude the urethra and prevent flow of urine past it. The open structure of the anti-migration cages 88 and 88' described herein do not prevent such urine flow and because they are made of tissue compatible soft plastic material, they do not materially irritate the urethral lining either during placement, removal or during prolonged periods of use.

FIG. 24 comprises a bladder drain like that of the embodiment of FIG. 16 but with the bladder retention means (curl segment 90 thereof) replaced with a differing style of retention member. As in the embodiment of FIG. 16, the urinary drain of FIG. 24 includes a flexible body member 78 having a proximal end 80 and a distal end 82. The body member 78 includes at least one channel 84 formed inwardly of the generally cylindrical surface thereof and it extends from the distal end 82 to a tapered zone 86 where the outside diameter of the drain body member 78 tapers to a lesser diameter where the drain body is void of any surface groove.

As in the embodiment of FIG. 16, there is affixed to the drain body 78 at a location that is a predetermined distance proximal of the tapered zone 86 an anti-migration cage 88 as has been previously described.

Located near the distal end of the bladder drain is a bladder retention means 133 that comprises first and second longitudinally spaced rows of radially-extending, soft, flexible petals that are generally equally circumferentially spaced about the periphery of the drain body 78. The petals in an upper row are angularly spaced and the petals in the row beneath it line up between adjacent petals on the upper row as is best seen in FIG. 25.

The bladder retention means 133 is preferably formed in a molding operation such that the leaves project radially from a central tubular member 132 (FIG. 25) such that attachment to the drain body 78 involves fitting the tube 132 over the drain body and bonding the tubular member 132 thereto.

To facilitate placement of the device of FIG. 24 into the urinary bladder, an outer sheath (not shown) may be employed. If a sheath is used, it would be slipped over the drain body 78, compressing the petals of the bladder retention means 133 against the surface of the drain body 78. Once the device has been advanced through the urethra to the point where the retention means 133 would be disposed within the urinary bladder, the outer sheath can be slipped off the drain, allowing the petals to spread and engage the bladder neck so as to resist expulsion of the drain device. Urine flows through the channel 84 as in the embodiment of FIG. 16 and the patient's sphincter cooperates with the portion of the tubular body member below the taper 86 to provide voluntary voiding of the bladder.

The petals comprising the retention means 133 are sufficiently flexible and pliable, however, that the application of tension forces to the tethers will cause the petals to fold up against the drain body as the device is withdrawn from the urethra.

The retention means 133 is preferably molded from a suitable plastic with a soft silicone rubber being preferred. The retention means, when unconstrained, may have a diameter of approximately one-half inch and the petals in each row may be spaced at 90 degree intervals.

In FIG. 26 there is shown a urinary drain in accordance with a further embodiment of the present invention. It includes a distal end portion 136 that comprises a soft, flexible plastic cylinder having a closed rounded distal end 138 and at least one and preferably more surface grooves 140 and 142 formed inwardly to provide channel(s) through which urine may flow. At the base of the distal end portion 136 is a bladder member 144 like that shown in FIG. 24. It includes first and second levels or rows of petals, such as four petals at 90 degree radial spacings. The petals in the upper row are offset 45 degrees from the petals in the lower row. The distal end portion 136 is bonded to a soft plastic tube 146 having a pattern of apertures 148 arranged in a spiral extending the length thereof. The tube 146 is dimensioned lengthwise to span the prostate gland in a male patient when the distal end portion 136 is resident within the urinary bladder and the petals of retention member 144 are engaging the bladder neck. Anchored to the lower end 150 of the tube 146 by webs 152 is a small diameter soft plastic tube 154 that extends across the urinary sphincter and through the urethra towards its meatus. As in the embodiment of FIGS. 16 and 24, an anti-migration cage 88 is affixed to the small diameter tube 154 so as to be immediately proximal of the patient's urinary sphincter. This enlargement or cage 88 cooperates with the urinary sphincter to prevent the device from longitudinally migrating in a distal direction.

The devices of FIGS. 24 and 26 are inserted in the same fashion as the drain device of FIG. 16 using a pusher member 94.

Once in place, urine contained in the bladder can flow through the channels or grooves 140 and 142 on the distal end portion 136 of the drain following such channels into the lumen of the tube 146. The presence of the apertures 148 allows secretions from the prostate gland to be washed away by urine flowing into and out of the apertures as it traverses the prostate. The outside diameter of the small diameter tube 154 spanning the sphincter allows the sphincter to close about the O.D. thereof, allowing voluntary voiding of the bladder. As mentioned, the anti-migration cage 88 is provided to prevent upward displacement of the drain assembly 134 within the urethra while the bladder retention petals 144 inhibit downward or proximal movement of the drain device.

Figure 28:
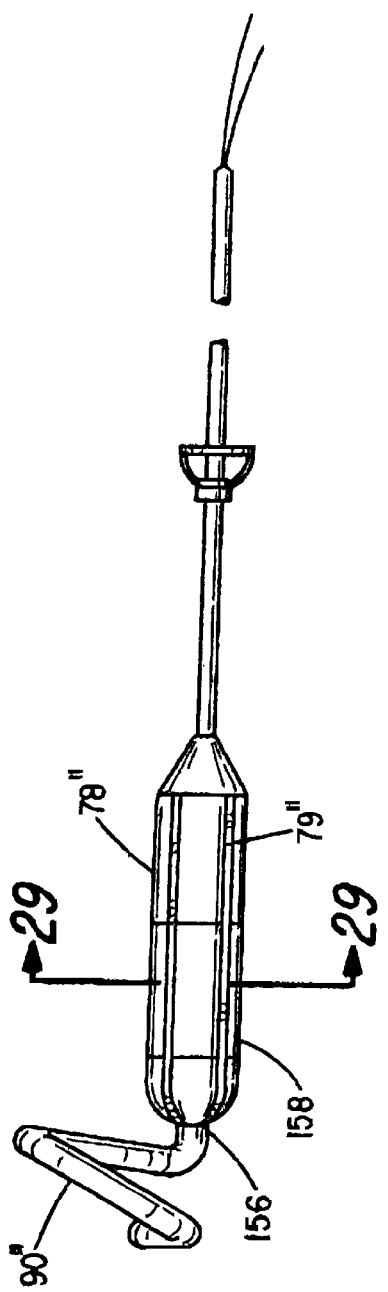
FIG. 28 is a side elevational view of an embodiment that is a variation of that shown in FIG. 21.
Figure 29:
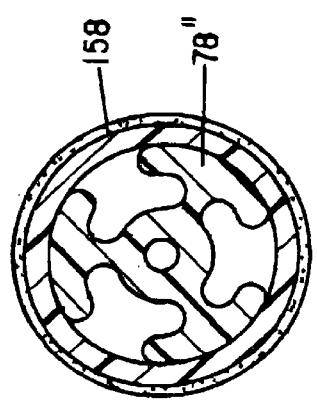
FIG. 29 is a cross-sectional view taken along the line 29—29 in FIG. 28.

The flexible, self-cleaning urethral drain illustrated in FIGS. 28 and 29 comprises a flexible, elongated drain body 78" formed from a soft elastomeric material such as silicone rubber. The exterior surface of the drain body includes at least one and preferably more than one open fluid drainage channel as at 79" extending substantially the entire length thereof. Affixed to the distal end of the drain body 78" is a bladder retention means that is preferably formed from a relatively small diameter tube that is preshaped such that when unconstrained by having a stiffening stylet inserted therein assumes a somewhat spiral shape with a portion of the retention means 90" extending below the upper rounded distal end 156 of the drain body 78". By thus forming the bladder retention curl 90", it is insured that the channels 79" will be exposed to the interior of the bladder when the retention device 90" is resident in the bladder neck.

To inhibit invagination of bladder neck tissue into the surface drainage channels 79", it may prove expedient to provide a thin plastic band 158 about the periphery thereof to prevent irritation to bladder neck tissue. Without the band, prostatic tissue may invaginate the surface channels 79" and with normal activity, contact between the drain body and the bladder neck may result in irritation. By providing the band 158, this irritation is minimized or avoided.

During certain surgical procedures and following radiation treatment for bladder cancer or the like, there is a propensity for tissue particles to sluff off from the bladder wall and these particles can result in blockage of the surface channels 79", preventing effective draining of urine from the bladder. To obviate this problem, a modification may be made as shown in FIG. 30. Here, rather than grinding a rounded tip on the drain body 78", the drain body is provided with a flat distal end 160 and affixed to it and at least partially surrounding the upper ends of the surface drainage channels 79" is a pre-formed plastic dome 162 having a series of fine slits 164 formed in it. Urine in the bladder may flow through the slits while particulate matter is blocked from flowing therethrough and into the surface channels 79". Again, the bladder retention device 90" is formed so that a portion thereof is at a level that is below the upper end of the dome 162 whereby the slits 164 reside above the bladder neck when the drain device is inserted through the urethra and properly positioned. A stiffening stylet as at 166 may be passed up through the drain body 78", the dome 162 and into the lumen of the tubular retention device 90" to render the bladder retention device rectilinear during placement of the drain.

In any of the disclosed embodiments, it may prove efficacious to coat the drain member with hydrogel to render it more soft and lubricious to aid in insertion thereof. The coating may also comprise a means for eluting a slow-release drug to combat urinary infection or to provide treatment to urinary organs when a suitable drug is incorporated into the coating.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A flexible, self-cleaning urethral drain for draining of urine and fluid from the bladder through the urethra of a patient, comprising:

(a) a flexible, elongated drain body having a distal end and a proximal end with an outer diameter allowing passage through the urethra, the drain body having an exterior surface with an open fluid drainage channel on at least a portion of said exterior surface, the drain body cooperating with the wall of the urethra for draining urine between the exterior surface of the drain body and the urethral wall;

(b) bladder retention means located adjacent to the distal end of the drain body for retaining the drain body in place in the urethra;

(c) means on the drain body for inhibiting longitudinal migration of said drain body relative to the urethral wall;

(d) a flexible tether affixed to the proximal end of the drain body of a length allowing the tether to extend out beyond the patient's urinary meatus when the bladder retention means is located in the patient's bladder;

(e) a tubular member of a diameter that can be inserted into the patient's urethra and removably secured to the proximal end of the drain body, the tubular member having an internal lumen for receiving the flexible tether therethrough; and (f) a removable clip member attachable to the tether at a point of exit of the tether from the proximal end of the tubular member, the clip being of a size greater than the diameter of the internal lumen of the tubular member.

2. The flexible, self-cleaning urethral drain as in claim 1 wherein said tether includes first and second separable segments where the length of the first separable segment is such that the first separable segment resides totally within the urethra when the bladder retention means is located in the patient's bladder.

3. The flexible, self-cleaning urethral drain as in any one of claims 1–2 wherein the means on the drain body for inhibiting longitudinal migration comprises:

a tubular body having a central bore for receiving a portion of the drain body therethrough, the tubular body being bonded to the drain body and including a plurality of integrally formed, regularly circumferentially spaced, rounded and tapered lobes, the lobes cooperating with the urethral wall proximal of the urinary sphincter when said urethral drain is in place in the urethra.

4. The urethral drain of claim 1 and further including means for eluting a drug from the exterior surface thereof.

5. The urethral drain of claim 1 and further including a lubricious coating on the exterior surface thereof.

6. The urethral drain of claim 1 wherein the lubricious coating comprises a hydrogel.

7. The urethral drain of claim 1 and further including an elutable drug contained in the lubricious coating.

8. A flexible, self-cleaning urethral drain for draining of urine and fluid from the bladder through the urethra of a patient, comprising:
   (a) a flexible, elongated drain body having a distal end and a proximal end with an outer diameter allowing passage through the urethra, the drain body having an exterior surface with an open fluid drainage channel on at least a portion of said exterior surface, the drain body cooperating with the wall of the urethra for draining urine between the exterior surface of the drain body and the urethral wall;
   (b) bladder retention means located adjacent to the distal end of the drain body for retaining the drain body in place in the urethra;
   (c) a bulbous, hollow, cage-like structure having a plurality of arcuate longitudinal ribs supporting an integrally formed annulus on a tubular base, said tubular base surrounding and affixed to a portion of said drain body and cooperating with the urethral wall proximal of the urinary sphincter when said urethral drain is in place in the urethra;
   (d) a flexible tether affixed to the proximal end of the drain body of a length allowing the tether to extend out beyond the patient's urinary meatus when the bladder retention means is located in the patient's bladder; and
   (e) a tubular member of a diameter that can be inserted into the patient's urethra and removably secured to the proximal end of the drain body, the tubular member having an internal lumen for receiving the flexible tether therethrough.

9. The flexible, self-cleaning urethral drain as in claim 8 wherein the cage-like structure is positioned on said portion of the drain body with the integrally formed annulus located distal of the tubular base, the annulus having an outer diameter greater than an outer diameter of the tubular base.

10. The urethral drain of claim 8 and further including means for eluting a drug from the exterior thereof.

11. The urethral drain of claim 8 and further including a lubricious coating on the exterior surface thereof.

12. The urethral drain of claim 8 wherein the lubricious coating comprises a hydrogel.

13. The urethral drain of claim 8 and further including an elutable drug contained in the lubricious coating.

14. A flexible, elongated drain body having:
   (a) a distal end and a proximal end with an outer diameter allowing passage through the urethra, the drain body having an exterior surface with an open fluid drainage channel extending longitudinally on said exterior surface, the drain body cooperating with the wall of the urethra for draining urine along the channel between the exterior surface of the drain body and the urethral wall;
   (b) bladder retention means located adjacent to the distal end of the drain body and adapted to cooperate with the bladder neck for retaining the drain body in place in the urethra, said bladder retention means being of a greater diameter than said outer diameter of the drain body;
   (c) a flexible tether affixed to the proximal end of the drain body, the tether being of a length allowing a portion thereof to extend out beyond the patient's urinary meatus when the bladder retention means is located in the patient's bladder neck; and
   (d) means on the drain body for inhibiting longitudinal migration of said body relative to the urethral wall.

15. The flexible, self-cleaning urethral drain as in claim 14 wherein said tether includes first and second separable segments where the length of the first separable segment is such that the first separable segment resides totally within the urethra when the bladder retention means is located in the patient's bladder.

16. The flexible, self-cleaning, urethral drain as in claim 15 wherein the bladder retention means comprises a plurality of circumferentially spaced, petal-like projections surrounding and affixed to the drain body.

17. The flexible, self-cleaning, urethral drain as in claim 16 wherein said plurality of petal-like projections are grouped into two longitudinally spaced rows, with the petal-like projections in the first of the two rows circumferentially offset from the petal-like projections in the other of the two rows.

18. The flexible, self-cleaning, urethral drain as in either of claim 16 or 17 wherein the petal-like projections are adapted to fold against the exterior surface of the drain body when being inserted and withdrawn from a patient's urethra.

* * * * *